(12) United States Patent
Petschow et al.

(10) Patent No.: US 8,021,708 B2
(45) Date of Patent: *Sep. 20, 2011

(54) METHOD FOR SIMULATING THE FUNCTIONAL ATTRIBUTES OF HUMAN MILK OLIGOSACCHARIDES

(75) Inventors: Byron W. Petschow, Newburgh, IN (US); Robert J. McMahon, Evansville, IN (US); Glenn R. Gibson, Reading (GB); Robert A. Rastall, Reading (GB); Renia Gemmell, Oxford (GB); Maria Saarela, Espoo (FI); Anna-Marja Aura, Espoo (FI)

(73) Assignee: Mead Johnson Nutrition Company, Evansville, IN (US)

( * ) Notice: Subject to any disclaimer, the term of this patent is extended or adjusted under 35 U.S.C. 154(b) by 183 days.

This patent is subject to a terminal disclaimer.

(21) Appl. No.: 12/370,141

(22) Filed: Feb. 12, 2009

(65) Prior Publication Data

US 2009/0176734 A1 Jul. 9, 2009

Related U.S. Application Data

(63) Continuation of application No. 11/172,123, filed on Jun. 30, 2005, now Pat. No. 7,572,474.

(51) Int. Cl.
*A23L 2/00* (2006.01)
*A61K 47/00* (2006.01)

(52) U.S. Cl. .......................... 426/590; 426/801; 424/439

(58) Field of Classification Search .................. 426/590, 426/801; 424/439
See application file for complete search history.

(56) References Cited

U.S. PATENT DOCUMENTS

| | | | |
|---|---|---|---|
| 4,859,488 A | 8/1989 | Kan et al. | |
| 5,437,880 A | 8/1995 | Takaichi et al. | |
| 5,840,361 A | 11/1998 | Theuer et al. | |
| 6,576,251 B1 | 6/2003 | Stahl et al. | |
| 6,706,287 B2 | 3/2004 | Ranganathan et al. | |
| 6,841,149 B1 | 1/2005 | Spangler et al. | |
| 7,572,474 B2 * | 8/2009 | Petschow et al. | 426/590 |
| 7,794,746 B2 * | 9/2010 | Gibson et al. | 424/439 |
| 2002/0127211 A1 | 9/2002 | Brassart et al. | |
| 2003/0040492 A1 | 2/2003 | Haschke et al. | |
| 2003/0060445 A1 | 3/2003 | Wilson | |
| 2003/0072865 A1 * | 4/2003 | Bindels et al. | 426/601 |
| 2003/0129278 A1 | 7/2003 | Stahl et al. | |
| 2003/0157146 A1 | 8/2003 | Rautonen et al. | |
| 2004/0062758 A1 | 4/2004 | Mayra-Makinen et al. | |
| 2004/0071824 A1 | 4/2004 | Van Laere et al. | |
| 2004/0072794 A1 | 4/2004 | Kaup et al. | |
| 2004/0077539 A1 | 4/2004 | Maase | |
| 2004/0121042 A1 * | 6/2004 | Kudo et al. | 426/43 |
| 2004/0161422 A1 | 8/2004 | Ranganathan | |
| 2004/0191234 A1 | 9/2004 | Haschke et al. | |
| 2004/0191295 A1 | 9/2004 | Locniskar et al. | |
| 2004/0219157 A1 | 11/2004 | Rochat et al. | |
| 2007/0009495 A1 * | 1/2007 | McMahon et al. | 424/93.7 |
| 2007/0207132 A1 * | 9/2007 | Speelmans et al. | 424/93.45 |

FOREIGN PATENT DOCUMENTS

| | | |
|---|---|---|
| CA | 2340103 | 2/2000 |
| WO | WO2004/112509 | * 12/2004 |
| WO | 2005039319 | 5/2005 |
| WO | 2005039597 | 5/2005 |

OTHER PUBLICATIONS

Craig, S.A.S., et al., Polydextrose as Soluble Fiber: Physiological and Analytical Aspects, Cereal Foods World, vol. 43, No. 5, p. 370-376, May 1998.
Moro, G., et al., Dosage-Related Bifidogenic Effects of Galacto- and Fructooligosaccharides in Formula-Fed Term Infants, J. Pediatr Gastroenterol Nutr, vol. 34, No. 3, Mar. 2002.
Roberfroid, M.B., Health benefits of non-digestible oligosaccharides, Adv Exp Med Biol. 1997;427:211-9. Review. PubMed PMID: 9361846. Abstract only.
Article online by Dairy Foods Magazine, Oct. 2003 by Donna Brooks entitled "Polydextrose for Adding Fiber." Online at http://www.dairyfoods.com.
Article by Chinese Medical Journal, 2004, vol. 117 No. 6, pp. 927-931 by X. Ben et al. entitled "Supplementation of milk formula with galacto-oligosaccharides improves intestinal micro-flora and fermentation in term infants." Online at http//www.cmj.org/information/full.asp?id=1655.
Article online by PDR health by S. Suphalac et al. entitled "Lactulose" pp. 1-5. Online at http//www.gettingwell.com/drug_info/nmdrugprofiles/ nutsuppdrugs/lac_0300.shtml.
Article by Current Pharmaceutical Design, 2005, vol. 11, pp. 55-74 by M.J. Kullen et al. entitled "The Delivery of Probiotics and Prebiotics to Infants.".
Article by Early Human Development, 2001, vol. 65 Suppl., pp. 43-52 by M. Rivero-Urgell et al. entitled "Olgiosaccharides: application in infant food.".
Article by American Journal Clinical Nutrition, 2001, vol. 73 Suppl., pp. 444-450 by E. Isolauri et al. entitled "Probiotics: effects on immunity 1-3.".
Article by American Journal Clinical Nutrition, 2001, vol. 73 Suppl., pp. 415-420 by J. Cummings et al. entitled "Prebiotics digestion and fermentation 1-3."
Article by American Society for Nutritional Sciences, Nutritional Immunology-Research Communication, 2003, pp. 153-156, by M. Roller et al. entitled "Prebiotic Inulin Enriched with Oligofructose in Combination with the Probiotic *Lactobacillus rhamnosus* and *Bifidobacterium lactis* Modulates Intestinal Immune Functions in Rats1."

(Continued)

*Primary Examiner* — Carolyn A Paden
(74) *Attorney, Agent, or Firm* — Waddey & Patterson, P.C.; James R. Cartiglia

(57) ABSTRACT

The present invention is directed to a novel method for increasing the production of acetate, decreasing the production of butyrate, increasing the population and species of beneficial bacteria and slowing the rate of fermentation of prebiotics within the gut of a formula-fed infant. The method comprises administration of a therapeutically effective amount of PDX to the infant.

19 Claims, 17 Drawing Sheets

OTHER PUBLICATIONS

Article from Journal of Medicinal Food, 2005, vol. 8(1), pp. 113-116 by Pylkans et al. entitled "Comparison of Different Fibers for in Vitro Production of short Chain Fatty Acids by Intestinal Microflora.".

Article by Applied and Environmental Microbiology, Aug. 2004, vol. 70, No. 8, pp. 4505-4511 by H. Probert et al. entitled "Polydextros, Lactitol, and Fructo-Oligosaccharide Fermentation by Colonic Bacteria in a Three-Stage Continuous Culture System.".

Article from Journal of Family Practice, Aug. 2002 by Mark R. Ellis entitled "What is the best therapy for constipation in infants?"—Clinical inquiries: from the Family Practice Inquiries Network. Online at http://www.findarticles.com/p/articles/mi_m0689/is_8_51/ai_90464039/print.

Article from Chinese Medical Journal, 2004, vol. 117 No. 6, pp. 927-931 by Ben Xiao-ming, et al. entitled Supplementation of milk formula with galacto-oligosaccharides improves intestinal microflora and fermentation in term infants. Online at http://www.Cmj.org/Periodical/PaperList.asp?id=LW8945.

Article from Am J Clin Nutr, 2000, vol. 72 pp. 1503-1509 by Zhong Jie, et al. entitled Studies on the effects of polydextrose intake on physiologic functions in Chinese people 1-3.

Article from Journal of Pediatric Gastroenterology and Nutrition, May 2001, vol. 32, pp. 534-541 by Tianan Jiang et al. entitled "Gas Production by Feces of Infants.".

Article from Journal of Pediatric Gastroenterology and Nutrition, Nov. 2004, vol. 39, pp. 465-473 by Carlo Agostoni, et al. entitled "Prebiotic Oligosaccharides in Dietetic Products for Infants: A Commentary" by the ESPGHAN Committee on Nutrition.

Article by Nutrition, 2002, vol. 18, pp. 484-489 by Pedro A. Alarcon et al. entitled "Gastrointestinal Tolerance of a New Infant Milk Formula in Healthy Babies: An International Study Conducted in 17 Countries.".

Article from J. Clin Gastroenteroal, Jul. 2004, vol. 38, Supp. 2 pp. S76-S79 by G. Boehm et al. entitled "Prebiotic in Infant Formulas.".

Article from Acta Paediatrica, 2005, vol. 94 (Suppl. 449), pp. 18-21 by Gunther Boehm et al. entitled "Prebiotic Carbohydrates in Human Milk and Formulas.".

Article from Arch. Dis. Child. Fetal Neonatal Ed., 2002, vol. 86, pp. F178-F181 by G. Boehm et al. entitled Supplementation of a bovine milk formula with an oligosaccharide mixture increases counts of faecal bifidobacteria in preterm infants. Online at http://www.bmj-journals.com.

ESPGHAN Abstracts by J. Pediatr Gastroenterology Nutr., Apr. 2003, vol. 36(4), No. P179 by G. Boehm et al. entitled Effect of increasing number of intestinal bifidobacteria on the presence of clinically relevant pathogens.

Article from Pediatrics, May 1993, vol. 91, No. 5, pp. 908-914 by Christi K. Bradley et al. entitled "Evaluation of Two Iron-Fortified, Milk-Based Formulas During Infancy.".

Article from Pediatric Research, 2006, vol. 59, No. 3, pp. 451-456 by Oscar Brunser et al. entitled "Effect of Milk Formula with Prebiotics on the Intestinal Microbiota of Infants After an Antibiotic Treatment.".

Article from Journal of Pediatric Gastroenterology and Nutrition, 2000, vol. 30, pp. 181-192 by Renee M. Erney et al. entitled "Variability of Human Milk Neutral Oligosaccharides in a Diverse Population.".

Article from Acta Paediatr, 2003, Supp. 441, pp. 48-55 by S. Fanaro et al. entitled "Intestinal Microflora in Early Infancy: Composition and Development.".

Article from Journal of Pediatric Gastroenterology and Nutrition, Aug. 2005, vol. 41, pp. 186-190 by S. Fanaro et al. entitled "Acidic Oligosaccharides from Pectin Hydrolysate as New Component for Infant Formulai: Effect on Intestinal Flora, Stool Characteristics, and pH.".

Article from J. Nutr., 1999, vol. 129, pp. 1438S-1441S by Glenn R. Gibson entitled "Dietary Modulation of the Human Gut Microflora Using the Prebiotics Oligofructose and Inulin.".

Article from J. Nutr., 1995, vol. 125, pp. 1401-1412 by Glenn R. Gibson et al. entitled "Dietary Modulation of the Human Colonic Microbiota: Introducing the Concept of Prebiotics.".

Article fromPediatrics, 1995, vol. 95, pp. 50-54 by Jeffrey S. Hyam et al. entitled "Effect of Infant Formula on Stool Characteristics of Young Infants.".

Article from Journal of Pediatric Gastroenterology and Nutrition, Mar. 2003, vol. 36, pp. 301-310 by Lawrence T. Weaver entitled "Improving Infant Milk Formulas: Near the End of the Trail for the Holy Grail?".

Article from Microbiol. Immunol., 1984, vol. 28, No. 9, pp. 975-986 by Yoshimi Benno et al. entitled "The Intestinal Microflora of Infants: Composition of Fecal Flora in Breast-Fed and Bottle-Fed Infants.".

ESPGHAN Abstracts from Journal of Pediatric Gastroenterology and Nutrition, Apr. 2002, vol. 34(4), p. 477, No. 2 by Knol et al. entitled "Bifidobacterial species that are present in breast fed infants are stimulated in formula fed infants by changing to a formula containing prebiotics.".

Article from Lipids, 1991, vol. 26, pp. 250-253 by R.J. Jandacek entitled "The Solubilization of Calcium Soaps by Fatty Acids.".

Article from Journal Clinical Microbiology, Feb. 1987, pp. 285-289 by Elisabeth A.E. Mevisen, et al. entitled "*Bifidobacterium*, *Bacteroides*, and *Clostridium* spp. In Fecal Samples from Breast-Fed and Bottle-Fed Infants with and without Iron Supplement.".

A book entitled Handbook of Milk Composition (1995) published by Academic Press, San Diego, Chapter 4, pp. 273-349, by David S. Newburg et al. entitled "Carbohydrates in Milks Analysis, Quantities and Significance.".

Article by The EFSA Journal, 2004, vol. 31, pp. 1-11 entitled "Opinion of the Scientific Panel on Dietetic Products, Nutrition and Allergies on a request from the Commission relating to the safety and suitability for particular nutritional use by infants of fructooligosaccharides in infant formulae and follow-on formulae.".

Article by Am J Clin Nutr, 1999, vol. 70, pp. 920-927 by Kathy Kennedy et al. entitled "Double-blind, randomized trial of a synthetic triacylglycerol in formula-fed term infants: effects on stool biochemistry, stool characteristics, and bone mineralization 1-3.".

ESPR Abstracts from J. Pediatr Gastroenterol Nutr., 2005, p. 487, Abstract No. 134 by C. van Limpt et al. entitled "Effect of Colonic Short Chain Fatty Acids, Lactate and pH on the Growth of Common Gut Pathogens.".

Article by Pediatrics, Jan. 1999, vol. 103, No. 1, pp. 1-6 by Beate Lloyd et al. entitled "Formula Tolerance in Postbreastfed and Exclusively Formula-fed Infants.".

Article by Acta Paediatr Scand., 1985, vol. 74, pp. 45-51 by B. Lundequest, et al. entitled "The Composition of the Faecal Microflora in Breastfed and Bottle Fed Infants from Birth to Eight Weeks.".

Article by BMJ, 1999, vol. 318, pp. 999-1003 by George T. Macfarlane et al. entitled "Probiotics and prebiotics: can regulating the activities of intestinal bacteria benefit health?".

A review published in Geneva 1994 by Gordon & Breach Science, pp. 90-106, Chapter 5 by Keisuke Matsumoto et al. entitled "Galactooligosaccharides.".

Article by Child: Care, Health and Development, 1997, vol. 23, No. 6, pp. 475-478 by R. Morley et al. entitled Infant Feeding and maternal concerns about stool harness.

Article by Acta Paediatr, 2003, Suppl. 441, pp. 77-79 by GE Moro, et al. entitled "Effects of a new mixture of prebiotics on faecal flora and stools in term infants.".

Article by Acta Paediatrica, 2005, vol. 94, Suppl. 449, pp. 27-30 by Guido Moro et al. entitled Dietary prebiotic oligosaccharides are detectable in the faeces of formula-fed infants.

Article by Acta Paediatr, 1999, Suppl. 430, pp. 47-57 by K. Orrhage et al. entitled "Factors controlling the bacterial colonization of the intestine in breastfed infants.".

Article by Journal of Pediatric Gastroenterology and Nutrition, 1995, vol. 20, pp. 81-90 by P.T. Quinlan et al. entitled "The Relationship between Stool Hardness and Stool Composition in Breast and Formula-Fed Infants.".

Article from Immunology and Medical Microbiology, 2005, vol. 43, pp. 59-65 by Minna M. Rinne et al. entitled "Similar bifidogenic effects of prebiotic-supplemented partially hydrolyzed infant formula and breastfeeding on infant gut microbiota.".

Article by Eur J. Nutr, 2002, vol. 41, pp. 85-92 by Silvia Rudloff et al. entitled "Detection of ligands for selectins in the oligosaccharide fraction of human milk.".

Article by Am J Clin Nutr, 2001, vol. 73 (Suppl.), pp. 459S-464S by Katharina E. Scholz-Ahrens et al. entitled "Effects of prebiotics on mineral metabolism.".

Abstract from PubMed by Indian J. Matern Child Health, 1993, vol. 4, No. 2, pp. 62-63 by K. Singh et al. entitled "Mothers' concept of the ideal number, colour and consistency of stools of their infants." Online at http://www.ncbi.nlm.nig.gov/entrez/query.fcgi?CMD=search&DB=pubmed.

Article by British Journal of Nutrition, 1999, vol. 81, pp. 121-132 by Jan Van Loo et al. entitled "Functional food properties of non-digestible oligosaccharides: a consensus report from the ENDO project (DGXII AIRII-CT94-1095).".

Article from J Nutr, 1979, vol. 109, pp. 1682-1687 by Fred H. Mattson et al. entitled "The absorbability by Rats of Various Triglycerides of Stearic and Oleic Acid and the Effect of Dietary Calcium and Magnesium." Online at http://jn.nutrition.org/cgi/content/abstract/109/10/1682.

* cited by examiner

Figure 6
Relative proportions of acetic acid, propionic acid and butyric acid and total SCFA production (average and S.D.) in the fermentation of Group 3 substrates.

|  |  | Acetic acid % | Propionic acid % | Butyric acid % | SCFA μmol Average |
|---|---|---|---|---|---|
| Time (h) | GOS |  |  |  |  |
| 0 |  | 79,3 | 8,6 | 12,1 | 144 |
| 1 |  | 86,5 | 5,6 | 7,8 | 354 |
| 2 |  | 89,5 | 4,6 | 5,9 | 727 |
| 4 |  | 86,3 | 5,7 | 8,0 | 1010 |
| 8 |  | 76,8 | 9,0 | 14,2 | 1134 |
| 24 |  | 67,1 | 15,7 | 17,2 | 1325 |
| Time (h) | LOS |  |  |  |  |
| 0 |  | 76,7 | 9,6 | 13,7 | 143 |
| 1 |  | 85,9 | 6,0 | 8,1 | 365 |
| 2 |  | 89,2 | 4,7 | 6,1 | 770 |
| 4 |  | 88,0 | 5,0 | 7,0 | 1104 |
| 8 |  | 77,0 | 7,0 | 16,1 | 1181 |
| 24 |  | 63,7 | 14,5 | 21,9 | 1359 |
| Time (h) | PDX2 |  |  |  |  |
| 0 |  | 77,8 | 9,2 | 13,1 | 156 |
| 1 |  | 83,1 | 7,1 | 9,8 | 303 |
| 2 |  | 81,2 | 7,6 | 11,2 | 426 |
| 4 |  | 75,7 | 9,9 | 14,4 | 550 |
| 8 |  | 74,3 | 12,5 | 13,2 | 775 |
| 24 |  | 66,5 | 23,3 | 10,2 | 1128 |
| Time (h) | FOS |  |  |  |  |
| 0 |  | 78,4 | 9,0 | 12,7 | 143 |
| 1 |  | 86,4 | 5,8 | 7,8 | 376 |
| 2 |  | 89,7 | 4,4 | 5,9 | 816 |
| 4 |  | 86,8 | 5,0 | 8,3 | 1195 |
| 8 |  | 77,7 | 7,4 | 15,0 | 1254 |
| 24 |  | 66,9 | 14,9 | 18,2 | 1470 |
| Time (h) | Fecal blank |  |  |  |  |
| 0 |  | 78,3 | 9,0 | 12,7 | 151 |
| 1 |  | 83,3 | 7,3 | 9,3 | 280 |
| 2 |  | 82,7 | 8,1 | 9,2 | 373 |
| 4 |  | 80,1 | 10,7 | 9,2 | 450 |
| 8 |  | 78,8 | 12,5 | 8,8 | 548 |
| 24 |  | 73,4 | 20,0 | 6,6 | 817 |

Figure 17

Summary of Prebiotic Effects on Fecal Microflora

| Test Prebiotic | Log10 increase with prebiotic (T12-T6) | | | | | | | |
|---|---|---|---|---|---|---|---|---|
| | Bifidobacteria | | Lactobacilli | | Clostridia | | Bacteroides | |
| | V1 | V2 | V1 | V2 | V1 | V2 | V1 | V2 |
| Human Milk | 1.34 | 2.13 | 1.66 | 1.87 | -1.00 | -2.55 | 0.09 | -0.12 |
| FOS | 1.55 | 0.05 | -1.26 | 0.26 | 1.14 | 0.71 | -0.48 | 0.97 |
| LOS | -0.50 | -0.28 | 0.70 | 1.19 | 0.11 | 1.22 | -0.59 | 0.20 |
| GOS | 0.33 | 0.75 | 0.00 | 0.00 | -1.31 | -0.15 | -0.85 | 0.03 |
| PDX | 0.23 | -0.17 | 1.35 | 0.55 | -1.79 | -0.88 | -1.64 | -1.79 |
| 1:1 PDX:GOS | 0.58 | 0.47 | 1.21 | 0.81 | 0.91 | 0.43 | 0.00 | 0.74 |
| 1:1 PDX:LOS | -0.32 | -0.33 | 0.57 | -0.25 | -0.22 | -0.10 | 0.12 | -0.41 |
| 1:1 LOS:GOS | 0.14 | 0.53 | 0.21 | 1.53 | 0.48 | -1.63 | -1.60 | 2.04 |

Note: V1 fermentation at pH=5.2; V2 fermentation at pH=6.7

METHOD FOR SIMULATING THE FUNCTIONAL ATTRIBUTES OF HUMAN MILK OLIGOSACCHARIDES

This application is a continuation of commonly assigned U.S. patent application Ser. No. 11/172,123, filed Jun. 30, 2005 now U.S. Pat. No. 7,572,474, the disclosure of which is incorporated herein in its entirety.

This application claims priority to U.S. Provisional Application 60/686,390 filed Jun. 1, 2005, which is incorporated by reference herein in its entirety.

BACKGROUND OF THE INVENTION (1) Field of the Invention

The present invention relates to a method for simulating the functional attributes of human milk oligosaccharides in infants.

(2) Description of the Related Art

The infant gut microflora is rapidly established in the first few weeks following birth. The nature of this intestinal colonization is initially determined by early exposure to environmental sources of microbes as well as the health of the infant. Whether the infant is breast-fed or formula fed also has a strong influence on the intestinal bacterial population.

In the breast-fed infant, for example, *Bifidobacterium* spp. dominate among intestinal bacteria, with *Streptococcus* spp. and *Lactobacillus* spp. as less common contributors. In contrast, the microflora of formula-fed infants is more diverse, containing *Bifidobacterium* spp. and *Bacteroides* spp. as well as the more pathogenic organisms, *Staphylococcus*, *Escherichia coli* and *Clostridium*. The varied species of *Bifidobacterium* in the stools of breast-fed and formula-fed infants differ as well.

Bifidobacteria are generally considered "beneficial" bacteria and ate known to protect against colonization by pathogenic bacteria. This likely occurs through competition for cell surface receptors, competition for essential nutrients, production of anti-microbial agents, and production of inhibitory compounds including short chain fatty acids (SCFA) which may decrease fecal pH and inhibit potentially pathogenic bacteria. *Bifidobacterium* spp. are also associated with resistance to gastrointestinal (GI) tract and respiratory infection as well as an enhanced immune function in children and infants. Therefore, the promotion of an intestinal environment in which bifidobacteria dominate has become a goal in the development of nutritional formulations for formula-fed infants.

Human milk (HM) contains a number of factors that may contribute to the growth and population of *Bifidobacterium* spp. in the gut microflora of infants. Among these factors is a complex mixture of more than 130 different oligosaccharides that reach levels as high as 812 g/L in transitional and mature milk. Kunz, et al., *Oligosaccharides in Human Milk: Structure, Functional, and Metabolic Aspects*, Ann. Rev. Nutr. 20: 699-722 (2000). These oligosaccharides are resistant to enzymatic digestion in the upper gastrointestinal tract and reach the colon intact, where they then serve as substrates for colonic fermentation.

HM oligosaccharides are believed to elicit an increase in the number of bifidobacteria in the colonic microflora, along with a reduction in the number of potentially pathogenic bacteria. Kunz, et al., *Oligosaccharides in Human Milk: Structure, Functional, and Metabolic Aspects*, Ann. Rev. Nutr. 20: 699-722 (2000); Newburg, *Do the Binding Properties of Oligosaccharides in Milk Protect Human Infants from Gastrointestinal Bacteria?*, J. Nutr. 217:S980-S984 (1997).

One way that HM oligosaccharides may increase the numbers of *Bifidobacterium* spp. and reduce the number of potentially pathogenic bacteria is by acting as competitive receptors and inhibiting the binding of pathogens to the cell surface. Rivero-Urgell, et al., *Oligosaccharides: Application in Infant Food*, Early Hum. Dev. 65(S):43-52 (2001).

In addition to reducing the number of pathogenic bacteria and promoting the population of bifidobacteria, when HM oligosaccharides are fermented, they produce SCFAs such as acetic, propionic and butyric acids. These SCFAs are believed to contribute to caloric content, serve as a major energy source for the intestinal epithelium, stimulate sodium and water absorption in the colon, and enhance small bowel digestion and absorption. In addition, SCFA are believed to contribute to overall gastrointestinal health by modulating gastrointestinal development and immune function.

The fermentation of HM oligosaccharides also reduces fecal ammonia, amine, and phenol concentrations, which have been implicated as the major odorous components of feces, as well as being toxic. Cummings & Macfarlane, *The Control and Consequences of Bacterial Fermentation in the Human Colon*, J. Appl. Bacteriol. 70:443-459 (1991); Miner & Hazen, *Ammonia and Amines: Components of Swine-Building Odor* ASAE 12:772-774 (1969); Spoelstra, *Origin of Objectionable Components in Piggery Wastes and the Possibility of Applying Indicator Components for Studying Odour Development*, Agric. Environ. 5:241-260 (1980); O'Neill & Phillips, *A Review of the Control of Odor Nuisance from Livestock Buildings Part 3. Properties of the Odorous Substances which have been Identified in Livestock Wastes or in the Air Around them* J. Agric. Eng. Res. 53:23-50 (1992).

As a result of the oligosaccharides present in HM, the SCFA profile of a breast-fed infant is very different from that of a formula-fed infant. For example, breast-fed infants produce virtually no butyrate, with acetate comprising approximately 96% of the total SCFA production. Lifschitz, et al., *Characterization of Carbohydrate Fermentation in Feces of Formula-Fed and Breast-Fed Infants*, Pediatr. Res. 27:165-169 (1990); Siigur, et al., *Faecal Short-Chain Fatty Acids in Breast-Fed and Bottle-Fed Infants*. Acta. Paediatr. 82:536-538 (1993); Edwards, et al., *Faecal Short-Chain Fatty Acids in Breast-Fed and Formula-Fed Babies*, Acta. Paediatr. 72:459-462 (1994); Parrett & Edwards, *In Vitro Fermentation of Carbohydrates by Breast Fed and Formula Fed Infants*, Arch. Dis. Child 76:249-253 (1997). In contrast, while formula-fed infants also have acetate (74%) as the major SCFA in feces, they have considerable amounts of propionate (23%) and small amounts of butyrate (3%) present as well. Such differences between the SCFA profiles of breast-fed infants and formula-fed infants could affect the energy, digestion, and overall health of the formula-fed infant.

Because cow's milk and commercially available infant formulas that are based on cow's milk provide only trace amounts of oligosaccharides, prebiotics are often used to supplement the diet of formula-fed infants. Prebiotics have been defined as "non-digestible food ingredients that beneficially affect the host by selectively stimulating the growth and/or activity of one or a limited number of bacteria in the colon that can improve the health of the host". Gibson, G. R. & Roberfroid, M. B., *Dietary Modulation of the Human Colonic Microbiota—Introducing the Concept of Probiotics*, J. Nutr. 125:1401-1412 (1995). Common prebiotics include fructo-oligosaccharides, galacto-oligosaccharides and lactulose.

The incorporation of various prebiotic ingredients into infant formulas has been disclosed. For example, U.S. Patent App. No. 20030072865 to Bindels, et al. discloses an infant formula with an improved protein content and at least one prebiotic. The prebiotic component can be lacto-N-tetaose, lacto-N-fuco-pentaose, lactulose (LOS), lactosucrose, raffinose, galacto-oligosaccharide (GOS), fructo-oligosaccharide (FOS), oligosaccharides derived from soybean polysaccharides, mannose-based oligosaccharides, arabino-oligo-saccharides, xylo-oligosaccharides, isomalto-oligo-saccharides, glucans, sialyl oligosaccharides, and fuco-oligosaccharides.

Similarly, U.S. Patent App. No. 20040191234 to Haschke discloses a method for enhancing the immune response which comprises administering at least one prebiotic. The prebiotic can be an oligosaccharide produced from glucose, galactose, xylose, maltose, sucrose, lactose, starch, xylan, hemicellulose, inulin, or a mixture thereof. The prebiotic can be present in an infant cereal.

Unfortunately, however, there are some disadvantages in the administration of the above prebiotics to formula-fed infants. While they may beneficially affect the population of probiotics in the gut, they do not produce a SCFA profile that is similar to that of a breast-fed infant. Additionally, the fermentation of many of these prebiotic substances occurs at a very rapid rate, which may produce excess gas, abdominal distension, bloating, and diarrhea. Therefore, the choice of prebiotic substances in infant formulas should be made with the goal of maximizing potential benefits and minimizing such unwanted side-effects.

Accordingly, it would be beneficial to provide a prebiotic substance that simulates the functional attributes of human milk oligosaccharides in infants, such as an increase in the population and species of beneficial bacteria in the infant gut and production of a SCFA profile similar to that of a breast-fed infant. Additionally, the prebiotic substance should be well tolerated in infants and should not produce or cause excess gas, abdominal distension, bloating or diarrhea.

SUMMARY OF THE INVENTION

Briefly, therefore, the present invention is directed to a novel method for simulating the functional attributes of human milk oligosaccharides in a formula-fed infant, the method comprising administering a therapeutically effective amount of polydextrose (PDX) to the infant.

The present invention is also directed to a novel method for increasing the population and species of beneficial bacteria in a formula-fed infant, the method comprising administering a therapeutically effective amount of PDX to the infant.

In another aspect, the present invention is directed to a novel method for producing a short-chain fatty acid (SCFA) profile in a formula-fed infant which is similar to that of a breast-fed infant, the method comprising administering a therapeutically effective amount of PDX to the infant. Specifically, PDX can cause the SCFA profile to have an increased level of acetate and a decrease in butyrate.

In yet another aspect, the present invention is directed to a novel method for decreasing the rate and extent of fermentation of prebiotics within the gut of a formula-fed infant, the method comprising administering a therapeutically effective amount of PDX to the infant. More particularly, the invention reduces the total gas production as well as the carbon dioxide production within the infant gut.

Among the several advantages found to be achieved by the present invention, it is well tolerated in infants and simulates the functional attributes of human milk oligosaccharides in infants, such as an increased population and species of beneficial bacteria in the infant gut, optimization of stool characteristics, and production of a SCFA profile similar to that of a breast-fed infant.

BRIEF DESCRIPTION OF THE DRAWINGS

For a more complete understanding of the present invention, reference is now made to the following descriptions taken in conjunction with the accompanying drawings.

FIG. 6 illustrates the relative proportions of acetic acid, propionic acid, butyric acid and total SCFA production in the fermentation of GOS, LOS, PDX and FOS.

FIG. 17 is a summary of the prebiotic effect of human milk, FOS, LOS, GOS, PDX, and various combinations thereof on fecal microflora.

DETAILED DESCRIPTION OF THE PREFERRED EMBODIMENTS

Figure 1:
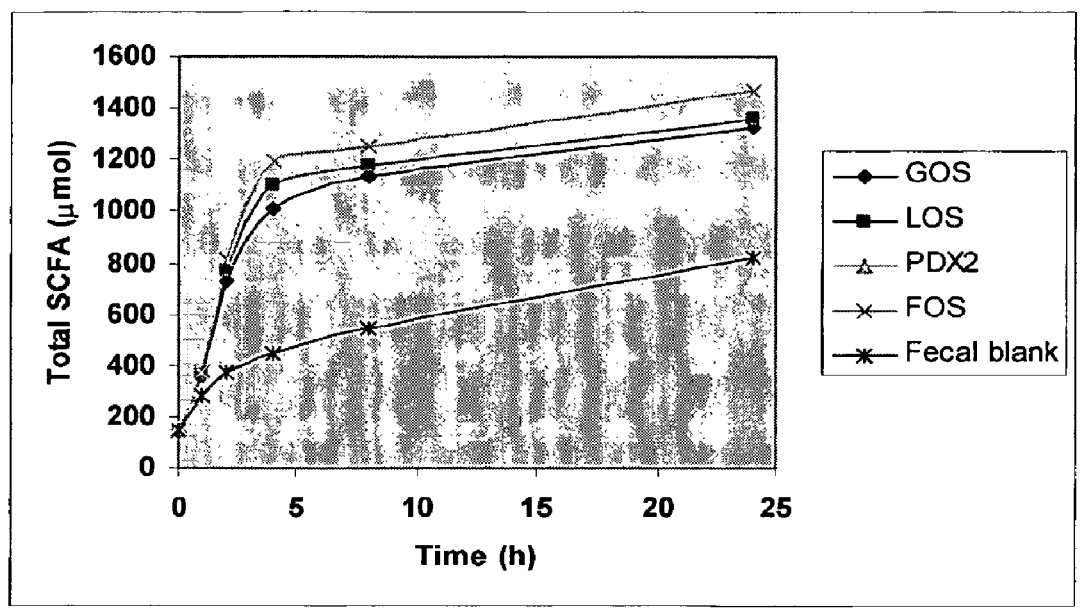
FIG. 1 illustrates total SCFA production during the fermentation of GOS, LOS, PDX2 and FOS.

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

DEFINITIONS

As used herein, the term "prebiotic" means a non-digestible food ingredient that beneficially affects the host by selectively stimulating the growth and/or activity of one or a limited number of bacteria in the colon that can improve the health of the host.

The term "probiotic" means a microorganism with low or no pathogenicity that exerts beneficial effects on the health of the host.

As used herein, the term "infant" means a human that is less than about one year old.

A "therapeutically effective amount", as used in the present application, means an amount that provides a prebiotic effect in the subject.

The term "simulating", as used herein means having or taking the form or appearance of or having or producing a symptomatic resemblance to.

The terms "functional attributes" mean any inherent quality or characteristic that causes something to occur. Examples of functional attributes of human milk oligosaccharides in the present invention can include the increase of the population and species of beneficial bacteria, production of a SCFA profile that is high in acetic acid and low in butyric acid, and production of a slow rate and low extent of fermentation of prebiotics in the gut.

As used herein, the term "infant formula" means a composition that satisfies the nutrient requirements of an infant by being a substitute for human milk. In the United States, the content of an infant formula is dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

Invention

In accordance with the present invention, a novel method for simulating the functional attributes of human milk oligosaccharides in formula-fed infants has been discovered. The method involves providing a therapeutically effective amount of PDX to the infant. The administration of PDX provides a beneficial effect on the population and species of probiotics, produces a SCFA profile that is similar to that of breast-fed infants and is physically well-tolerated by infants.

PDX is a non-digestible carbohydrate that has been synthesized from randomly cross-linked glucose and sorbitol. It is not digested in the upper GI tract and is only partially fermented in the lower GI tract, making it a beneficial ingredient for digestive health. The physiological benefits of PDX include increased fecal bulk, reduced transit time, lower fecal pH and reduced concentration of putrefactive substances in the colon. In adults, PDX ingestion has also been shown to aid in the promotion and growth of beneficial bacteria in the intestine and production of SCFAs.

PDX has been identified as a prebiotic substance for adults based on its functions in the GI tract. For example, U.S. Patent App. No. 20040062758 to Mayra-Makinen, et al. relates to a composition which comprises a probiotic and one or more prebiotics, where the prebiotic can be GOS, palatinoseoligosaccharide, soybean oligosaccharide, gentiooligosaccharide, xylooligomers, nondegradable starch, lactosaccharose, LOS, lactitol, maltitol, or PDX. Similarly, U.S. Pat. No. 4,859,488 to Kan relates to a liquid food comprising PDX and oligosaccharides that is useful for curing constipation.

PDX has hot, however, been identified as a prebiotic that provides the benefits of the present invention and can be administered to infants. The gut microflora of infants is well known to be less developed than that of an adult. While the microflora of the adult human consists of more than $10^{13}$ microorganisms and nearly 500 species, the gut microflora of an infant contains only a fraction of those microorganisms, both in absolute number and species diversity. Because the bacterial populations and species vary immensely between the gut of an infant and an adult, it cannot be assumed that a prebiotic substance that has a beneficial effect on adults would also have a beneficial effect on infants.

In adults, PDX ingestion has been shown to increase the production of acetate and butyrate. Because butyrate is not noted in appreciable levels in breast-fed infants and has been associated with harmful effects if produced at significant levels in the infant intestine, PDX would not generally be considered appropriate for infant nutrition based on its observed effects in the adult GI system. Thus, it was surprising and unexpected that PDX was actually metabolized primarily to acetate and propionate, with little butyrate formation. Thus, not only did PDX have a positive impact on the population and species of beneficial bacteria in the infant intestinal tract, but it also created a SCFA profile that was very similar to that of a breast-fed infant and would be extremely well-tolerated by infants.

One particular reference that relates to PDX in the context of infant administration actually teaches the converse of the present invention. In U.S. Patent App. No. 20030157146 to Rautonen, it is asserted that PDX can stimulate the immune system of infants. In that application, however, the Applicant discloses that PDX actually decreased the population of *Bifidobacterium* spp. in the infant gut (Rautonen App., para. 0074). Applicant justifies this result by noting that "an abundance of bifidobacteria may cause also less desirable physiological effects such as enteric bacterial diseases and immunosuppression." (Rautonen App., para. 0069).

Because the reference teaches that PDX actually decreases the population of bifidobacteria in the infant gut, it is in direct conflict with the teaching of the present application. Additionally, the reference does not demonstrate that PDX increases the production of acetate, decreases the production of butyrate or decreases the rate of fermentation of prebiotics within the infant gut.

In the methods of the present invention, a therapeutically effective amount of PDX is administered to an infant for the purpose of simulating the functional attributes of human milk oligosaccharides. A therapeutically effective amount of PDX may be between about 1.0 g/L and 10.0 g/L, administered daily. In another embodiment, a therapeutically effective amount of PDX may be between 2.0 g/L and 8.0 g/L, administered daily.

PDX is commercially available from a variety of sources. For example, STA-LITE® PDX is available in 5 lb bags from Honeyville Grain, Inc., located in Salt lake City, Utah. Alternatively, Litesse® Ultra™ PDX is commercially available from Danisco Sweeteners, Ltd., located in the United Kingdom.

PDX is well-suited for incorporation into an infant formula, as it contains only 1 Cal/g, as compared to 4 Cal/g for typical prebiotics. It is also highly soluble and neutral tasting. Therefore, its addition to infant formula would not change the physical or taste characteristics of the composition.

The form of administration of PDX in the method of the invention is not critical, as long as a therapeutically effective amount is administered. Most conveniently, the PDX is supplemented into infant formula which is then fed to an infant.

The infant formula for use in the present invention is preferably nutritionally complete and typically contains suitable types and amounts of lipid, carbohydrate, protein, vitamins and minerals. The amount of lipid or fat typically can vary from about 3 to about 7 g/100 kcal. The amount of protein typically can vary from about 1 to about 5 g/100 kcal. The amount of carbohydrate typically can vary from about 8 to about 12 g/100 kcal. Protein sources can be any used in the art, e.g., nonfat milk, whey protein, casein, casein protein, soy protein, hydrolyzed protein, amino acids, and the like. Carbohydrate sources can be any used in the art, e.g., lactose, glucose, corn syrup solids, maltodextrins, sucrose, starch, rice syrup solids, and the like. Lipid sources can be any used in the art, e.g., vegetable oils such as palm oil, soybean oil, palmolein, coconut oil, medium chain triglyceride oil, high oleic sunflower oil, high oleic safflower oil, and the like.

Conveniently, commercially available infant formula can be used. For example, Enfalac, Enfamil®, Enfamil® Premature Formula, Enfamil® with Iron, Lactofree®, Nutramigen®, Pregestimil®, or ProSobee® (available from Mead Johnson & Company, Evansville, Ind., U.S.A.) may be supplemented with suitable levels of PDX and used in practice of the method of the invention.

In an embodiment of the present invention, PDX can be administered in combination with another prebiotic. The prebiotic selected can be any prebiotic known in the art. Examples of prebiotics include, but are not limited to: FOS, inulin, gluco-oligosaccharide, GOS, isomalto-oligosaccharide, xylo-oligosaccharide, soybean oligosaccharides, chito-oligosaccharide, gentio-oligosaccharide, manno-oligosacchaide, LOS, lactosucrose, raffinose, aribino-oligosaccharide, glucans, siallyl-oligosaccharide, and fuco-oligosaccharide.

In a particular embodiment of the present invention, PDX is administered in combination with GOS. GOS is a mixture of oligosaccharides consisting of D-glucose and D-galactose. It is sometimes referred to as trans-galacto-oligosaccharide. It is produced from D-lactose by β-galactosidase, which can be obtained from *Aspergillus oryzae*. GOS has been suggested to increase calcium absorption and prevention of bone loss in adults. GOS has been identified as a prebiotic that is useful for administration to infants in U.S. Patent App. No. 20030072865 to Bindels, et al.

In this embodiment, PDX and GOS can be administered in a ratio of PDX:GOS of between about 9:1 and 1:9. In another embodiment, the ratio of PDX:GOS can be between about 5:1 and 1:5. In yet another embodiment, the ratio of PDX:GOS can be between about 1:3 and 3:1. In a particular embodiment, the ratio of PDX to GOS can be about 5:5. In another particular embodiment, the ratio, of PDX to GOS can be about 8:2.

A therapeutically effective amount of the PDX:GOS combination may be between about 1.0 g/L and 10.0 g/L, administered daily. In another embodiment, a therapeutically effective amount of the PDX:GOS combination may be between about 2.0 g/L and 8.0 g/L, administered daily. In a particular embodiment, a therapeutically effective amount of the PDX:GOS combination may be about 2 g/L of PDX and 2 g/L of GOS, administered daily.

In another specific embodiment of the present invention, PDX is administered in combination with LOS. LOS is a semisynthetic disaccharide formed from D-galactose and D-fructose and joined by a β-glucosidic linkage. It is resistant to hydrolysis by human digestive enzymes, but is fermented in the small intestine. It is highly soluble and has a sweet taste. LOS has been identified as a prebiotic that is useful for administration to infants in U.S. Patent App. No. 20030072865 to Bindels, et al., LOS is commercially available from a variety of sources.

In this embodiment, PDX and LOS can be administered in a ratio of between about 9:1 and 1:9. In another embodiment, the ratio of PDX to LOS can be between about 5:1 and 1:5. In yet another embodiment, the ratio of PDX to LOS can be between about 3:1 and 1:3. In a particular embodiment, the ratio of PDX to LOS can about 5:5. In another particular embodiment, the ratio of PDX to LOS can be about 8:2.

A therapeutically effective amount of the PDX:LOS combination may be between about 1.0 g/L and 10.0 g/L, administered daily. In another embodiment, a therapeutically effective amount of the PDX:LOS combination may be between about 2.0 g/L and 8.0 g/L, administered daily. In a particular embodiment, a therapeutically effective amount of the PDX:LOS combination may be about 2 g/L of PDX and 2 g/L of LOS, administered daily.

In yet another embodiment of the present invention, PDX is administered in combination with both GOS and LOS. In this embodiment, the PDX:GOS:LOS combination can be administered in a ratio of about 50:33:17. Alternatively, the ratio of the PDX:GOS:LOS combination can be about 1:1:1. In a particular embodiment, the ratio of PDX:GOS:LOS can be about 1:1.5:1.

A therapeutically effective amount of the PDX:GOS:LOS combination may be between about 1.0 g/L and 10.0 g/L, administered daily. In another embodiment, a therapeutically effective amount of the PDX:GOS:LOS combination may be between about 2.0 g/L and 8.0 g/L, administered daily. In an embodiment, a therapeutically effective amount of the PDX:GOS:LOS combination may be about 2 g/L PDX, 2 g/L GOS and 2 g/L LOS, administered daily. In a particular embodiment, a therapeutically effective amount of the PDX:GOS:LOS combination may be about 2 g/L PDX, 1.32 g/L GOS and 2.6 g/L LOS, administered daily. In another embodiment, a therapeutically effective amount of the PDX:GOS:LOS combination may be about 4 g/L PDX, 2.64 g/L GOS and 3.6 g/L LOS, administered daily.

In one embodiment of the invention, PDX can be combined with one or more probiotics and administered to an infant. Any probiotic known in the art will be acceptable in this embodiment. In a particular embodiment, the probiotic is chosen from the group consisting of *Bifidobacterium* spp. or *Lactobacillus* spp. In an embodiment, the probiotic is *Lactobacillus rhamnosus* GG (LGG) (ATCC number 53103). In another embodiment, the probiotic is *Bifidobacterium lactis*. In a specific embodiment, the probiotic is *Bifidobacterium lactis* Bb-12, available from Chr. Hansen Biosystems, located in Milwaukee, Wis.

In other embodiments of the present invention, the infant formula may contain other active agents such as long chain polyunsaturated fatty acids (LCPUFA). Suitable LCPUFAs include, but are not limited to, α-linoleic acid, γ-linoleic acid, linoleic acid, linolenic acid, eicosapentaenoic acid (EPA), arachidonic (ARA) and docosahexaenoic acid (DHA). In an embodiment, PDX is administered in combination with DHA. In another embodiment, PDX is administered in combination with ARA. In yet another embodiment, PDX is administered in combination with both DHA and ARA. Commercially available infant formula that contains DHA, ARA, or a combination thereof may be supplemented with PDX and used in the present invention. For example, Enfamil® LIPIL®, which contains effective levels of DHA and ARA, is commercially available and may be supplemented with LGG and utilized in the present invention.

In one embodiment, both DHA and ARA are administered in combination with PDX. In this embodiment, the weight ratio of ARA:DHA is typically from about 1:3 to about 9:1. Alternatively, this ratio can be from about 1:2 to about 4:1. In yet another alternative, the ratio can be from about 2:3 to about 2:1. In one particular embodiment the ratio is about 2:1.

The effective amount of DHA in an embodiment of the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

The effective amount of ARA in an embodiment of the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

The amount of DHA in infant formulas for use with the present invention typically varies from about 5 mg/100 kcal to about 80 mg/100 kcal. In one embodiment of the present invention it varies from about 10 mg/100 kcal to about 50 mg/100 kcal; and in another embodiment from about 15 mg/100 kcal to about 20 mg/100 kcal. In a particular embodiment of the present invention, the amount of DHA is about 17 mg/100 kcal.

The amount of ARA in infant formulas for use with the present invention typically varies from about 10 mg/100 kcal to about 100 mg/100 kcal. In one embodiment of the present invention, the amount of ARA varies from about 15 mg/100 kcal to about 70 mg/100 kcal. In another embodiment the amount of ARA varies from about 20 mg/100 kcal to about 40 mg/100 kcal. In a particular embodiment of the present invention, the amount of ARA is about 34 mg/100 kcal.

The infant formula supplemented with oils containing DHA and ARA for use with the present invention can be made using standard techniques known in the art. For example, they can be added to the formula by replacing an equivalent amount of an oil, such as high oleic sunflower oil, normally present in the formula. As another example, the oils containing DHA and ARA can be added to the formula by replacing an equivalent amount of the rest of the overall fat blend normally present in the formula without DHA and ARA.

The source of DHA and ARA can be any source known in the art. In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils. DHA and ARA can be in natural or refined form.

In one embodiment, the source of DHA and ARA is substantially free of eicosapentaenoic acid (EPA). For example, in one embodiment of the present invention the infant formula contains less than about 16 mg EPA/100 kcal; in another embodiment less than about 10 mg EPA/100 kcal; and in yet another embodiment less than about 5 mg EPA/100 kcal. One particular embodiment contains substantially no EPA. Another embodiment is free of EPA in that even trace amounts of EPA are absent from the formula.

The infant formula of the present invention can be prepared using any method known in the art. In one embodiment, the PDX is provided in powder form. It can be mixed with water and other infant formula ingredients in a mixing tank. If GOS and/or LOS are included in the infant formula, they can be provided in powdered or liquid form. The mixture can then be pasteurized, homogenized and spray-dried to make a finished powder or canned and retorted to make a liquid product.

As an alternative to an infant formula administration, the prebiotic of the present invention can be administered as a supplement not integral to the formula feeding. For example, PDX can be ingested in the form of a pill, tablet, capsule, caplet, powder, liquid or gel. In this embodiment, the PDX can be ingested in combination with other nutrient supplements, such as vitamins, or in combination with a LCPUFA supplement, such as DHA or ARA.

In another embodiment, PDX can be provided in a form suitable for infants selected from the group consisting of follow-on formula, beverage, milk, yoghurt, fruit juice, fruit-based drink, chewable tablet, cookie, cracker, or a combination thereof.

In the method of the present invention, the infant is formula-fed. In one embodiment the infant is formula-fed from birth. In another embodiment, the infant is breast-fed from birth until an age which is less than one year, and is formula-fed thereafter, at which time PDX supplementation begins.

Human milk oligosaccharides can increase the population and species of beneficial bacteria in the intestinal tract, have a SCFA profile that is high in acetate and very low in butyrate, and are slowly fermented, avoiding the production of excessive gases. As will be seen in the examples, the administration of PDX, alone or in combination with other prebiotics, can be used to increase the population and species of beneficial bacteria in the intestinal tract, may preferentially shift the SCFA production toward more acetate and propionate production, thereby limiting butyrate production, and can slow down the fermentation rate in the gut so that gas production is limited, minimizing discomfort to the infant. Thus, the administration of PDX, alone or in combination with one or more other prebiotics, can simulate the functional attributes of human milk oligosaccharides in a formula-fed infant.

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

Example 1

This example illustrates the in vitro fecal fermentation model utilized in the present Invention. The fecal fermentation model in vitro mimics the action of the colon microbiota of infants. During fermentation, carbohydrates are consumed and SCFA and gases are produced. After fermentation, an analysis of the effect of the prebiotics on the populations and genera of microorganisms present can be accomplished.

The individual carbohydrates which were studied are set forth in Table 1.

TABLE 1

Individual Carbohydrates

GOS: Vivinal GOS: Deb. No. 00026961 Borculo Domo Ingredients; received Sep. 17, 2002; purity 95.1%
LOS: Morinaga Lactulose Anhydride: MLC-A(F), Lot No. FRDL020926; Morinaga Milk Industry Co. Ltd; received Oct. 4, 2002; purity 97%
PDX: Sta-Lite III PDX: Lot No. DZ2K0351913; A.E. Staley
FOS: Raftilose P95 Fructo-oligosaccharides: Lot No. PCAB022B02; Raffinerie Notre-Dame/Orafti SA; received Sep. 6, 2002; Purity 95.1%
PDX2: Litesse ® Ultra ™ PDX: high molecular-weight polymer, max 22 000 MW; Danisco; Lot No. V36020I
INU: Raftiline ® HP: long-chain inulin DP $\geq$ 23 (Lot no hptoh11oh1; Orafti B.V.; received October 2002; D.S. 96.9%, Inulin 99.9%, Sucrose + Fructose + Glucose 0.1%).

Fecal samples were collected from healthy infants aged 2.5-13 months. Five experimental groups were run, using different combinations of prebiotic carbohydrates in each fermentation group. Twelve babies were recruited for the Group 1 and 2 fermentations, 17 babies for the Group 3 fermentation, 19 babies for the Group 4 fermentation and 23 babies for the Group 5 fermentation. In groups 1-3, only five babies were able to donate an acceptable sample. The babies recruited for the first fermentation were 4, 4, 4, 6, 6, 6, 8, 8, 9, 9, 9 and 10 months of age, for the second fermentation 3, 4, 6, 6, 6, 7, 8, 9, 10, 10, 12 and 13 months of age, and for the third fermentation 2, 2.5, 3, 4, 4, 4, 4.5, 5, 5, 6, 6, 6, 9, 9, 10, 10 and 11 months of age. The ages of the babies whose samples were used in the fermentation were Group 1: 6, 8, 9, 9, 9 months; Group 2: 4, 8, 10, 12, 13 months; and Group 3: 2.5, 5, 6, 10, 11 months. In the Group 4 fermentation, 10 babies (of which one baby twice) were able to donate an acceptable sample. The donors for the Group 4 fermentation were 2, 2.5, 4, 5, 7, 9, 9, 10, 11 and 15 months of age. For the Group 5 fermentation, twelve babies were able to donate samples, of which the four youngest donors were selected. Thus, the donors were 5, 6, 6.5 and 6.5 months of age.

Fecal fermentation in vitro was performed according to the method of Karppinen, which is hereby incorporated by reference in its entirety. Karppinen S., et al., *In Vitro Fermentation of Polysaccharides of Rye, Wheat, and Oat Brans and Inulin by Human Faecal Bacteria*, J. Sci. Food Agric. 80:1469-76 (2000).

In the present study, 100 mg of carbohydrate samples were weighed into 50 ml bottles and hydrated using 2 ml of carbonate-phosphate buffer at pH 6.9. The samples were kept overnight under anaerobic conditions at 5° C. until preparation of the inoculum. Fecal slurry (12.5%, weight/volume) was prepared under strictly anaerobic conditions in the same buffer by pooling freshly voided infant feces. Eight ml of the suspension was dosed to the substrate samples and bottles closed in an anaerobic chamber giving the final fecal slurry concentration of 10% (weight volume). Samples were incubated at 37° C. for 1, 2, 4, 8 or 24 hours. 0 hour samples were prepared similarly to the centrifugation tubes and frozen rapidly using liquid nitrogen. Fecal blanks without added carbohydrates were included in all fermentation experiments.

Fermentation was finished by removing the bottles from the waterbath and placing them on ice except prior to gas measurement, when samples were kept at room temperature for immediate sampling. Gas volume was measured and gas sample (5 ml) was injected to a nitrogenated headspace bottle. The bottle was placed on ice after the sampling. The fermentation sample was transferred to a centrifugation tube, pH was measured and an aliquot (2 ml) was drawn from the slurry for SCFA analysis and frozen rapidly with liquid nitrogen.

Example 2

This example illustrates the materials and methods necessary to determine the effectiveness of polydextrose as a prebiotic for formula-fed infants. Specifically, this example illustrates the materials and methods necessary to analyze SCFAs and gases.

SCFAs were extracted with diethyl ether and analyzed with gas chromatography as described by Karppinen, et al., which is hereby incorporated by reference in its entirety. Karppinen S., et al., *In Vitro Fermentation of Polysaccharides of Rye, Wheat, and Oat Brans and Inulin by Human Faecal Bacteria*, J. Sci. Food Agric. 80:1469-76 (2000). Gases (hydrogen, carbon dioxide, methane, hydrogen disulfide, and oxygen as a quality control) were analyzed isothermally at 30° C. using a static headspace technique by gas chromatography according to Karppinen, et al. Id.

Example 3

Figure 2:
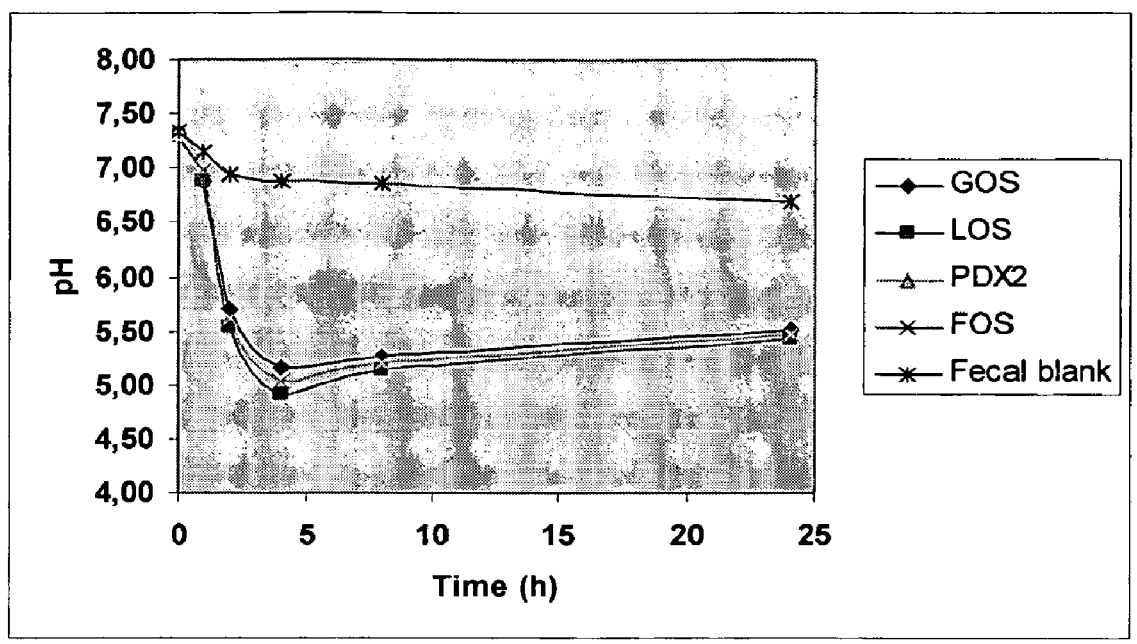
FIG. 2 illustrates pH changes during the fermentation of GOS, LOS, PDX2 and FOS.

This example illustrates the effect of PDX on the in vitro SCFA profile produced by the infant colon microbiota. FIGS. 1 and 2 illustrate that the rate of fermentation varies among different prebiotics. The production of total SCFA (a sum of acetic, propionic and butyric acids) is shown in FIG. 1. A decrease in pH, shown in FIG. 2, is also an indication of SCFA production.

As can be seen in the figures, PDX2 is a slowly fermentable carbohydrate, whereas FOS, GOS and LOS were fermented fast and completely. The fermentation rate of PDX2 was comparable to cereal dietary fibers. Not only was PDX2 fermented at the slowest initial rate, but the extent of fermentation was only slightly above the fecal blank. In contrast, the fermentation rate of FOS was so rapid that it was consumed almost completely within the first-sampling time points and produced the highest amount of SCFAs among prebiotics tested.

Figure 3:
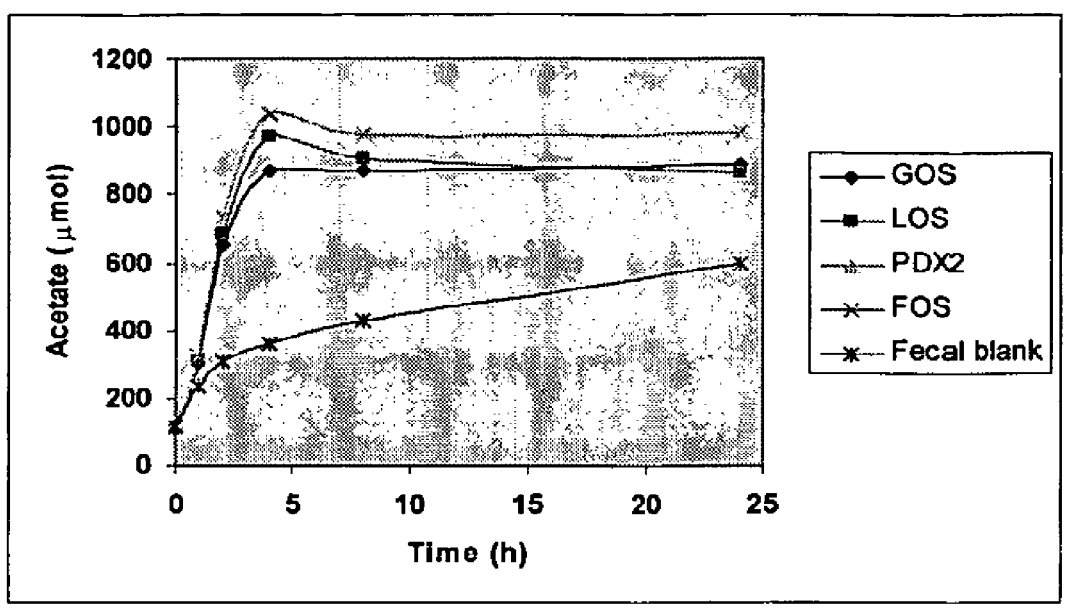
FIG. 3 illustrates the relative proportion of acetic acid production in the fermentation of GOS, LOS, PDX2 and FOS.
Figure 4:
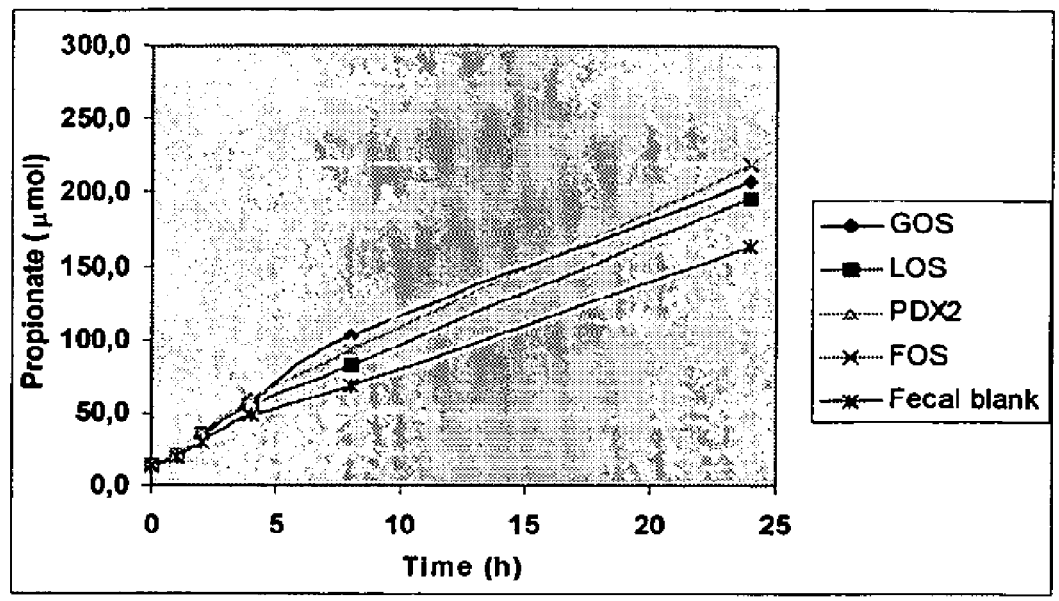
FIG. 4 illustrates the relative proportion of propionic acid production in the fermentation of GOS, LOS, PDX2 and FOS.
Figure 5:
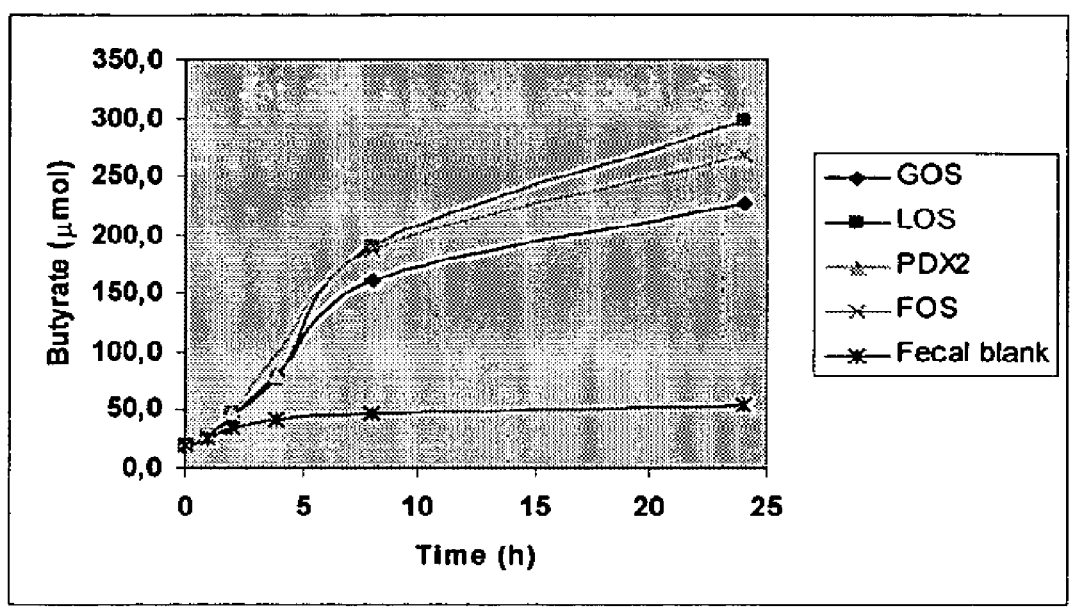
FIG. 5 illustrates the relative proportion of butyric acid production in the fermentation of GOS, LOS, PDX2 and FOS.

As shown in FIG. 3-5, PDX2 fermentation results in the highest propionate production and the lowest butyrate production after 24 hours. Acetate was still the highest SCFA produced during the fermentation of PDX, although the initial rate was much lower than those of the other substrates. The initial rate of propionate production from PDX2 was similar to that of the other substrates, but higher levels were found at the end of fermentation. In contrast, the fermentation of FOS, GOS and LOS showed increased concentrations of acetate and butyrate and decreased concentration of propionate. As a result, the combined relative proportion of acetate and propionate was much higher for PDX2 than for FOS, LOS or GOS. These results can also be seen in FIG. 6. These results demonstrate that PDX2 was the least butyrate-producing substrate and the only substrate for increasing the relative proportion of propionate.

These results are in agreement with an in vitro study conducted by Wang, X. & Gibson, G. R., *Effects of the In Vitro Fermentation of Oligofructose and Inulin by Bacteria Growing in the Human Large Intestine*, J. Appl. Bacteriol. 75:373-

380 (1993), in which fecal slurry from adult donors was used in the fermentation of various carbohydrates. However, the higher propionate production from POX in vitro was not shown in vivo in a clinical trial with Chinese adults. Jie, Z., et al., *Studies on the Effects of Polydextrose Intake on Physiological Functions in Chinese People*, Am. J. Clin. Nutr. 72:1503-09 (2000), in which three different PDX concentrations could increase the levels of butyrate and acetate, but not the proportion of propionate. Larger production of butyrate from GOS and FOS has also been shown with human fecal flora associated rats (Djouzi, Z., et al., *Compared Effects of Three Oligosacchardies on Metabolism of Intestinal Microflora in Rats Inoculated with a Human Faecal Flora*, Br. J. Nutr. 78:313-24 (1997).

Example 4

This example illustrates the effect of combinations of prebiotics on the in vitro fermentation rate by infant colon microbiota. Various combinations of prebiotic carbohydrates were chosen in an attempt to achieve a desirable rate of microbial fermentation in vitro. In this example, the substrate combinations were compared for their fermentation rate (total SCFA production) and changes in pH, shown in FIGS. 7-8.

Figure 7:
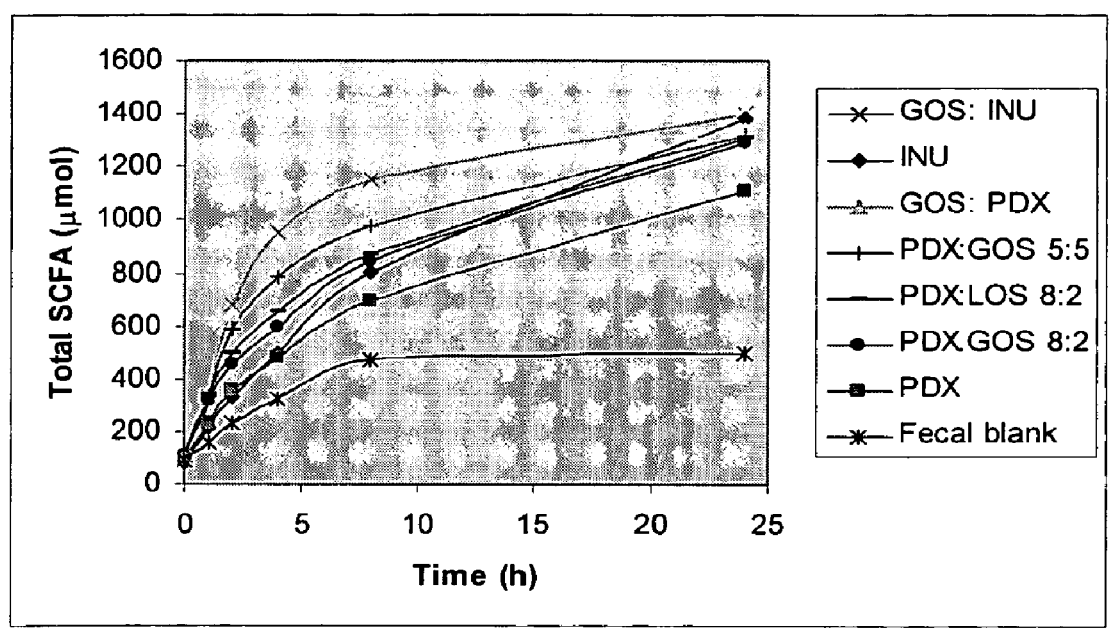
FIG. 7 illustrates the total SCFA production during the fermentation of various combinations of prebiotic carbohydrates.
Figure 8:
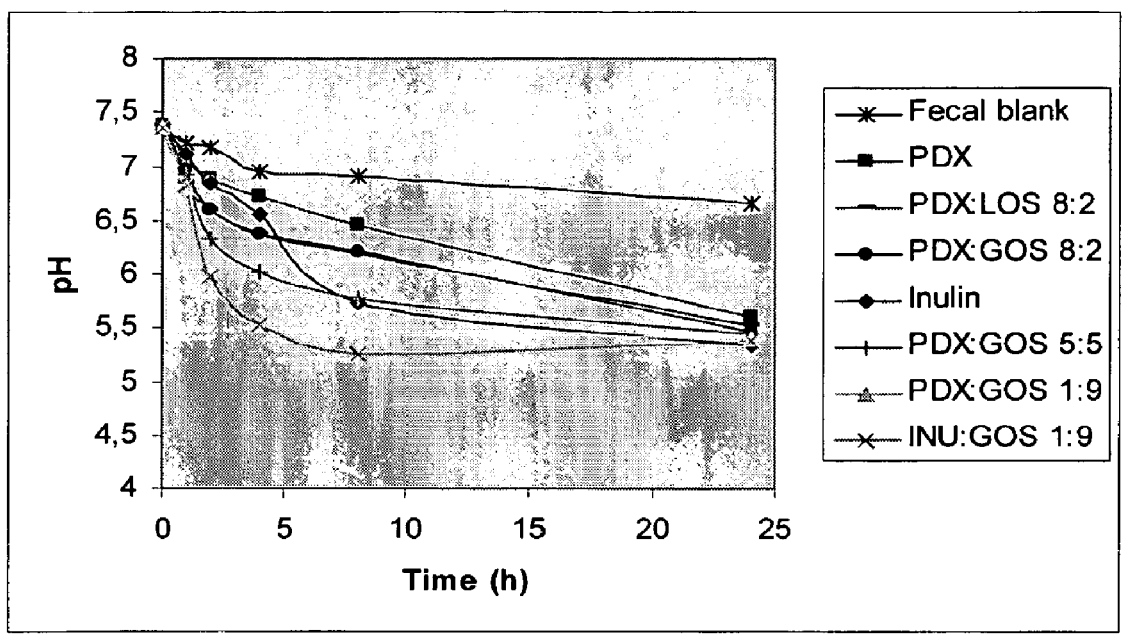
FIG. 8 illustrates the pH changes during the fermentation of various combinations of prebiotic carbohydrates.

The addition of PDX to the GOS preparation slowed the fermentation rate of the combination as measured by total SCFA production (FIG. 7). Similarly, the addition of PDX to the LOS preparation slowed the fermentation rate of the combination. The addition of PDX to LOS or GOS also resulted in a more moderate decrease in pH, as shown in FIG. 8. This slower rate of acidification of stool content may lead to less irritation of the intestinal lining or anal region, increasing infant tolerance. The slower decrease in pH by PDX is consistent with slower SCFA production and overall in vitro fermentation rate compared to GOS and LOS. These results demonstrate that PDX can be used to slow down the fermentation rate of the mixtures of PDX and traditional prebiotics such as GOS or LOS.

Figure 9:
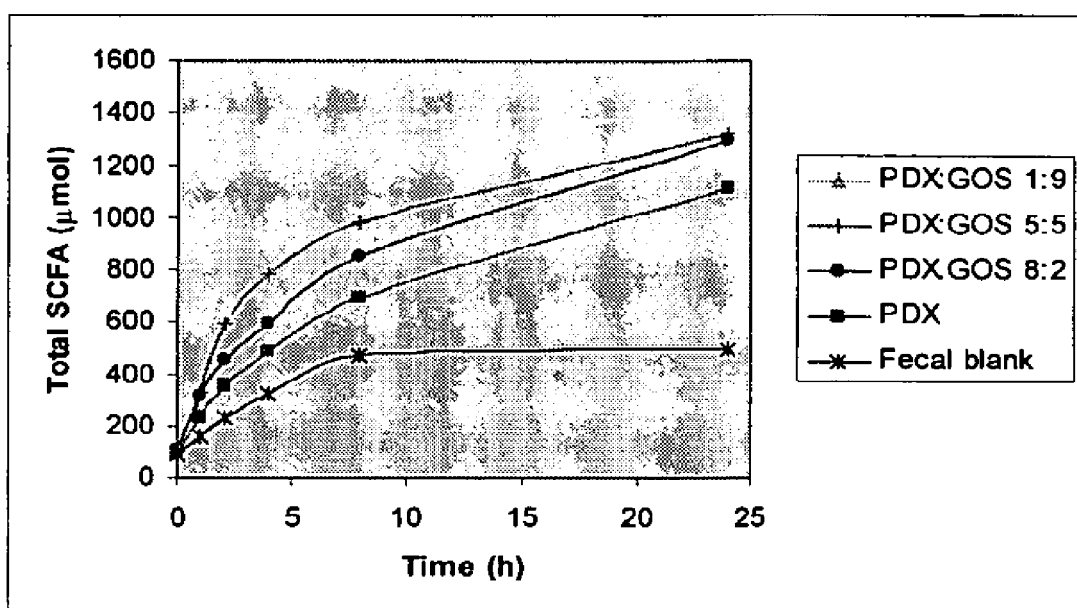
FIG. 9 illustrates the total SCFA production during the fermentation of different combinations of PDX and GOS.
Figure 10:
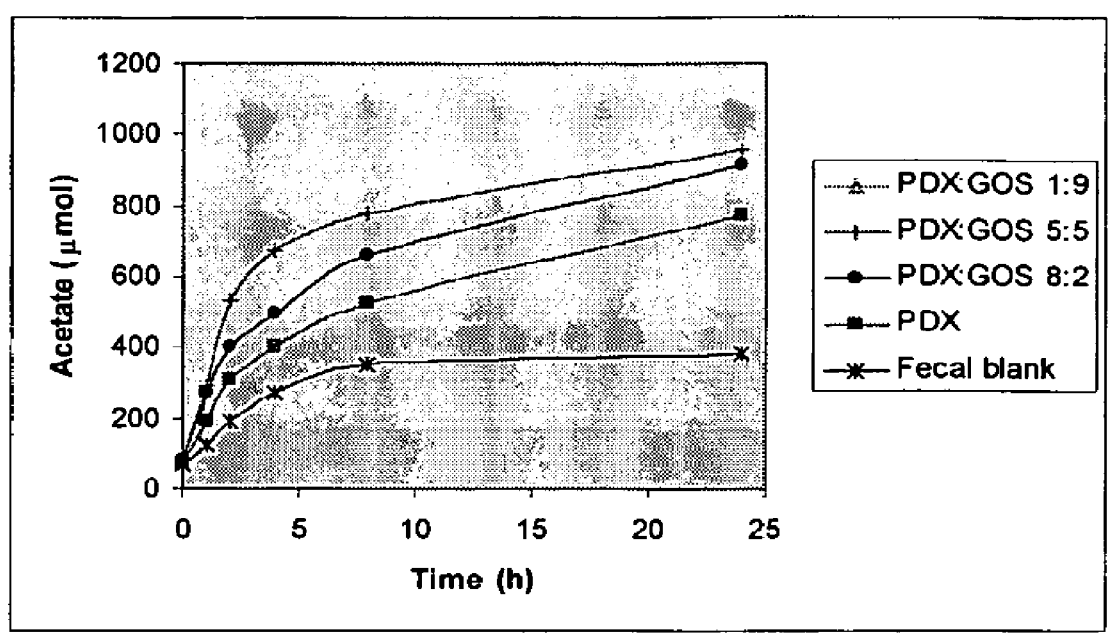
FIG. 10 illustrates the concentration of acetic acid produced during the fermentation of different combinations of PDX and GOS.
Figure 11:
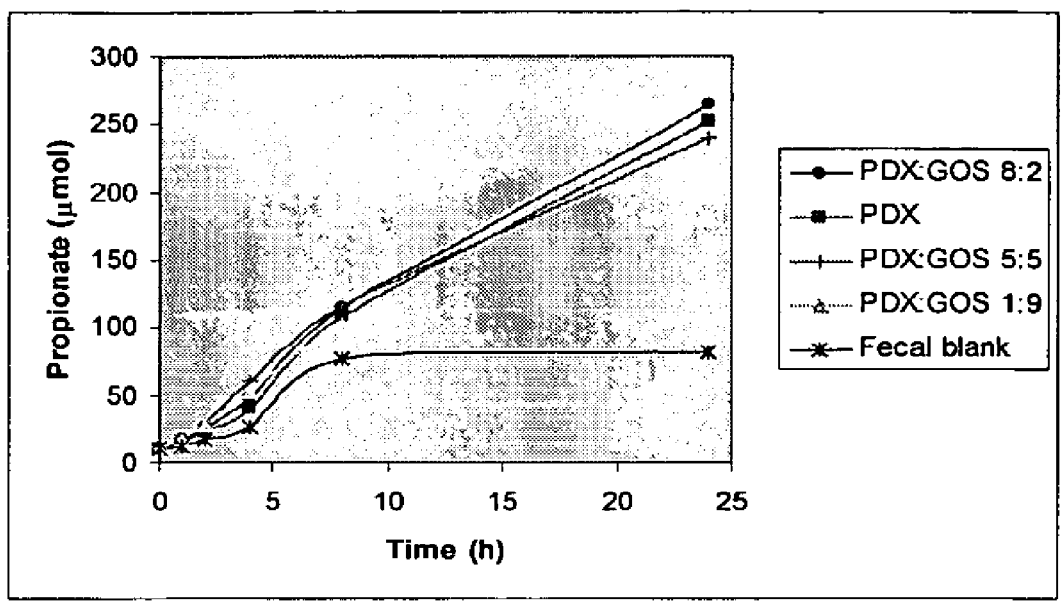
FIG. 11 illustrates the concentrations of propionic acid produced during the fermentation of different combinations of PDX and GOS.
Figure 12:
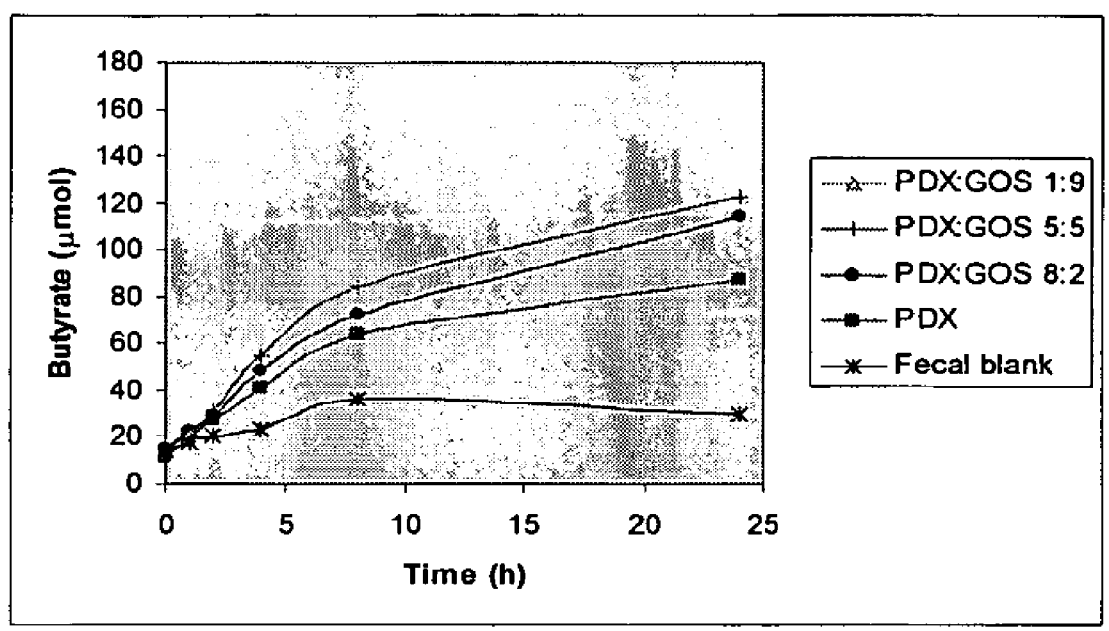
FIG. 12 illustrates the concentration of butyric acid produced during the fermentation of different combinations of PDX and GOS.

The effect of the PDX:GOS ratio on the production of total SCFA, acetate, propionate and butyrate was also studied (FIGS. 9-12). FIG. 9 demonstrates that a PDX:GOS ratio of 8:2 led to a slower rate of total SCFA production than did a PDX:GOS ratio of 5:5. FIG. 9 confirms that a PDX:GOS ratio of 8:2 produced less total SCFA than a ratio of 5:5 or 1:9. Thus, these results demonstrate that a higher amount of PDX in the PDX:GOS mixture results in a slower rate of fermentation in vitro. The addition of PDX to GOS also had the tendency to decrease the rate of acetate and butyrate production, but had little impact on the overall rate and final propionate production.

Example 5

Figure 13:
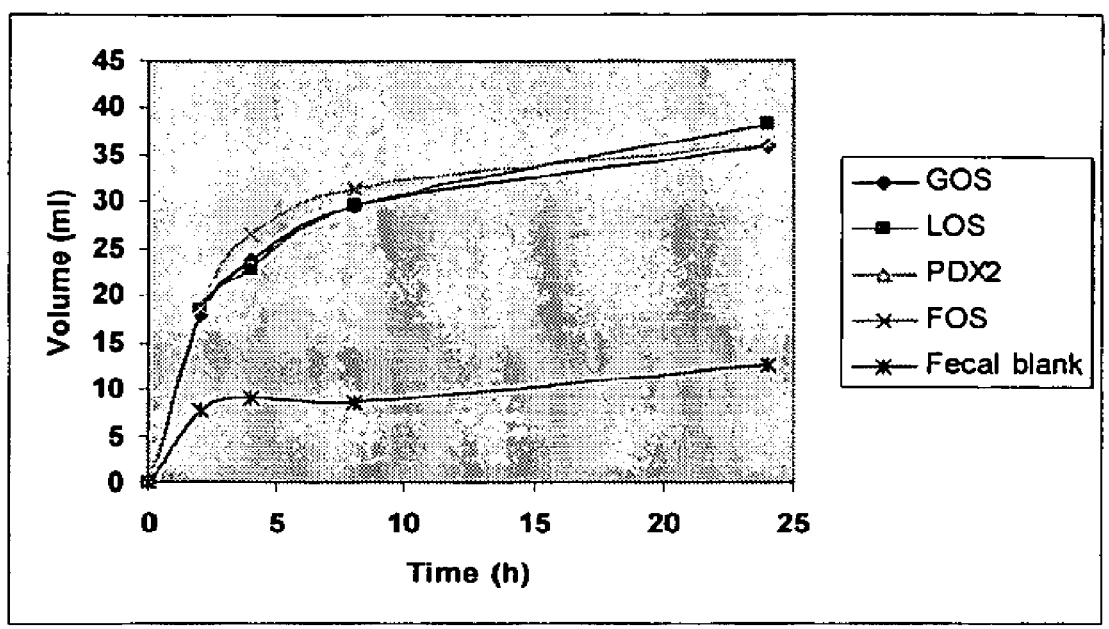
FIG. 13 illustrates the formation of gases as total volume during the fermentation of GOS, LOS, PDX2 and FOS.

This example illustrates the effect of PDX on in vitro gas production by infant colon microbiota. Total gas production, measured as the total volume per fermentation bottle, was about equal with GOS, LOS and FOS, shown in FIG. 13. In contrast, PDX results in lower overall gas production during fermentation by infant fecal bacterial microbiota. The lower overall gas production seen in POX also indicates that it is fermented more slowly than the other prebiotics studied.

In addition to total gas production, carbon dioxide production is an important measure of infant tolerance to dietary prebiotics. The major gas product of all prebiotics tested was carbon dioxide. It was produced in 3- and 44-76-fold higher amounts than hydrogen or hydrogen sulphide, respectively.

Figure 14:
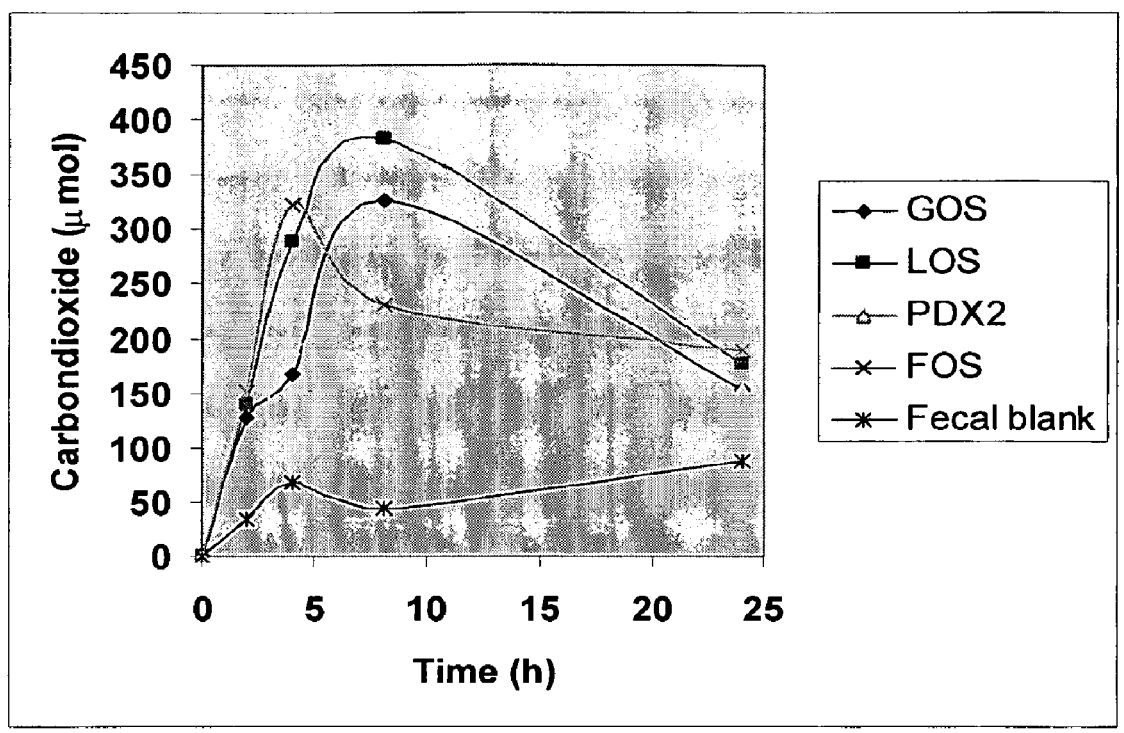
FIG. 14 illustrates the formation gases as carbon dioxide concentration during the fermentation of GOS, LOS, PDX2 and FOS.
Figure 15:
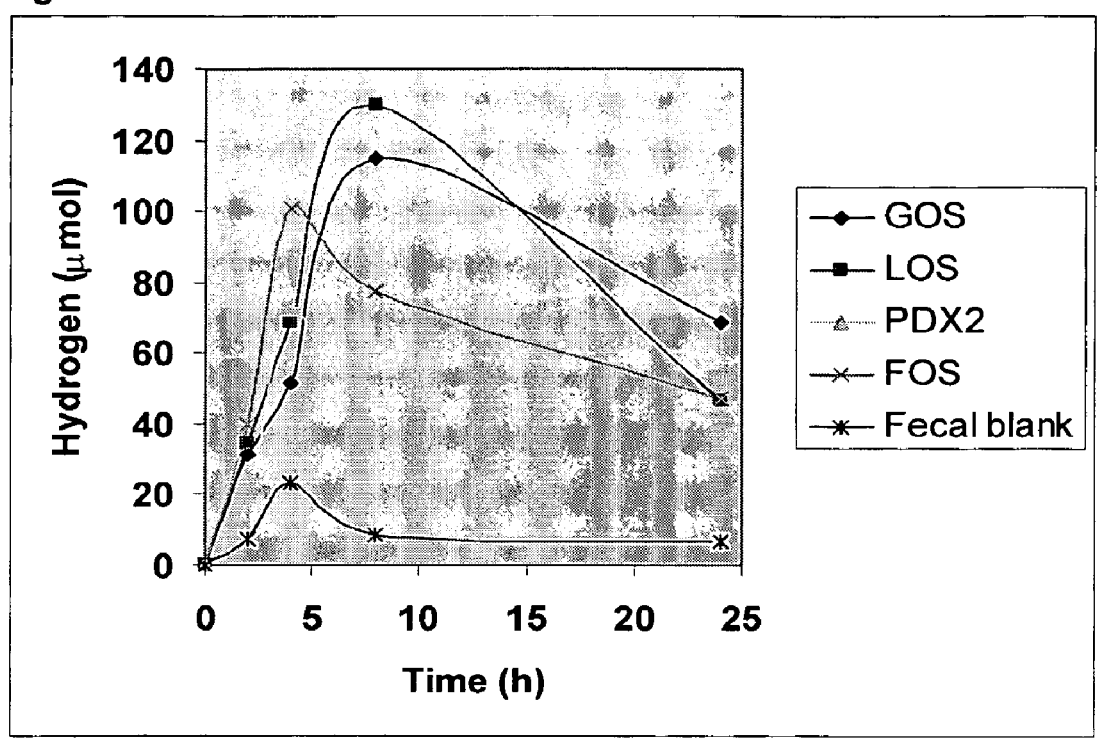
FIG. 15 illustrates the formation of gases as hydrogen concentration during the fermentation of GOS, LOS, PDX2 and FOS.
Figure 16:
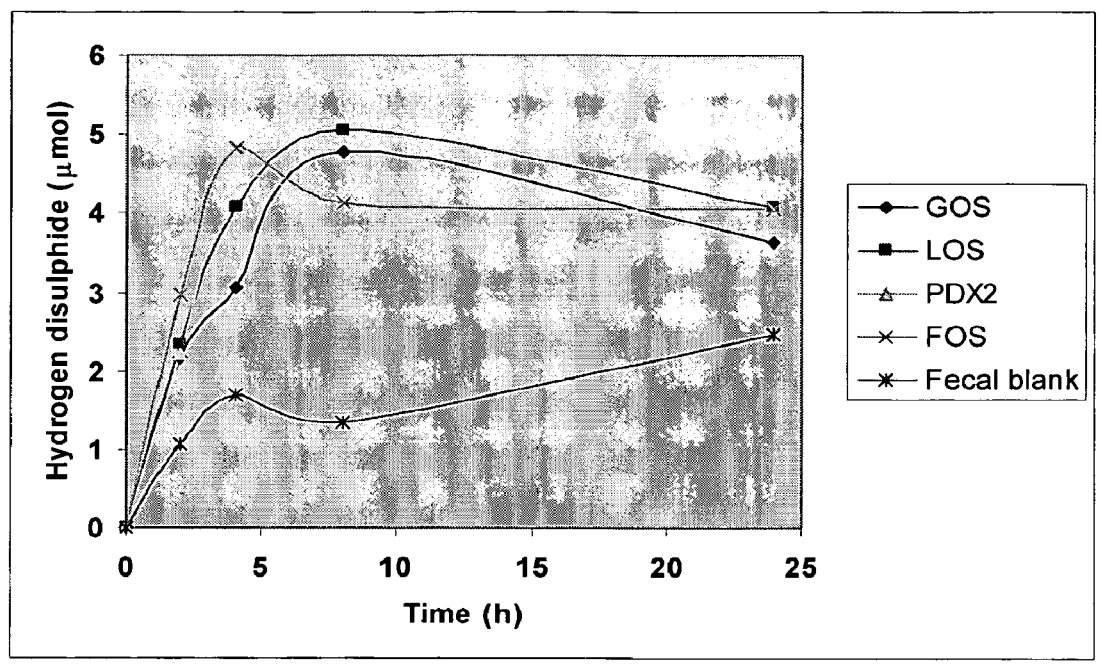
FIG. 16 illustrates the formation of gases as hydrogen disulphide concentration during the fermentation of GOS, LOS, PDX2 and FOS.

Overall, production of carbon dioxide was the lowest for POX when compared with FOS, GOS and LOS (FIG. 14). Carbon dioxide was the ran a gas produced during the fermentation of FOS, GOS and LOS, showing maximum levels between 320-380 μmol. In contrast, PDX showed much lower levels of carbon dioxide formation (200 μmol). Hydrogen formation from POX by infant fecal microbiota was lower (about one third) than carbon dioxide production, and considerably lower than levels of hydrogen produced from FOS, GOS and LOS (FIG. 15). Hydrogen sulphide formation from PDX was 1:44 compared to the formation of carbon dioxide and maximal hydrogen sulphide production was at about the same level of concentration for all test prebiotics (FIG. 16). The larger proportion of carbon dioxide formation compared to the formation of hydrogen (1000-fold) and methane (10-fold) was also shown by Wang and Gibson. Wang, X. & Gibson, G. R., *Effects of the In Vitro Fermentation of Oligofructose and Inulin by Bacteria Growing in the Human Large Intestine*, J. Appl. Bacteriol. 75:373-380 (1993). Since methanogenesis was not observed in the present study, hydrogen disulphide was formed presumably from primary hydrogen Levitt, et al., *Gas Metabolism in the Large Intestine*, CRC Press, Boca Raton 131-154 (1995). It is possible that hydrogen was not detected due to its further metabolism to secondary gas, hydrogen disulphide, at late time points.

Example 6

This example illustrates the materials and methods necessary to determine the effect of PDX on the population and species of microbiota from the infant colon. Briefly, the example utilizes an infant gut model to evaluate certain prebiotic compounds. The infant gut in vitro model utilized, which was based on an adult version, was comprised of two 100 ml glass vessels, arranged in series to represent the proximal and distal regions of the infant colon. The feed flow was controlled at a rate that took into account the shorter passage lime in the infant gut, as compared to an adult gut. To model in vivo differences in pH within the colon, vessel 1 (V1) was controlled at pH 5.2 and vessel 2 (V2) was controlled at pH 6.7. Temperature was controlled at 37° C. by a circulating water bath. The feed and culture vessels were magnetically stirred and maintained under an anaerobic atmosphere by inflowing oxygen-free nitrogen (15 mL/min).

Once the system was inoculated with infant fecal slurry, the two fermenter vessels were left for up to 24 hours in batch mode. This allowed the bacterial populations to equilibrate in their new environment and increase in density. The feed flow was then turned on and the fermenter ran in continuous culture mode for the remainder of the experiment. The feed flow rate was controlled at 11.11 ml/h. In this study, the fermenters were run for 12 days, 6 days being fed Enfalac infant formula (Mead Johnson Nutritionals, Evansville, Ind.) and a further 6 days being fed Enfalac and the added prebiotic or prebiotic combination.

Samples of 5 ml were then taken aseptically from V1 and V2 and prepared for the culture, independent microbial enumeration procedure Fluorescence In Situ Hybridisation (FISH) and microscopy for the identification and enumeration of specific bacterial species. Use of FISH allows the accurate determination of the effect of prebiotics on specific bacterial populations in the proximal and distal regions of the infant colon.

Prebiotics were added to the feed individually or in combinations, at a total concentration of 7.5 g/l (0.75% w/v). The following oligosaccharides were used:

TABLE 2

Prebiotics Tested

| Prebiotic | Type | Manufacturer |
|---|---|---|
| Lactulose (LOS) | Syrup | Morinaga Milk Ind. Co. Ltd., Japan |
| Galacto-oligosaccharide (GOS) | E0002 powder | Supplied by Mead Johnson |
| Polydextrose (PDX) | 'Litesse Ultra' powder | Danisco |
| Fructo-oligosaccharide | Raftilose ® P95 powder | Orafti |

The infant donors were carefully selected and ideally aged 24 months, formula-fed (exclusively where possible), healthy and not under recent antibiotic treatment. A minimum age of 2 months was preferred as the infant gut microbiota is established by this age.

TABLE 3

Donor Information

| Donor Code | Age | Feed | Fermentation Run |
|---|---|---|---|
| KB | 16 weeks | SMA Gold | F1 |
| JS | 13 weeks | Cow & Gate | F2 |
| F | 19 weeks | SMA Gold and breast-fed | F3 |
| AE | 9½ weeks | breast fed | F4 |
| AE | 14 weeks | breast fed | F5 |

The microbial flora of the infant gut for fermentation tests was provided by freshly voided infant feces. A fecal sample of at least 3.5 g was usually required. The fecal sample was retained in the diaper which, immediately on removal from the infant, was placed by the caregiver into an anaerobic jar with an opened anaerobic gas pack. This was collected and processed as soon as possible (usually within the hour).

In the laboratory, the feces were removed from the diaper and weighed. A 10% (w/v) fecal slurry was prepared by homogenizing the samples in anoxic and pre-warmed (overnight in the anaerobic cabinet) 1×PBS solution, using a stomacher at medium rate for 120 seconds.

Each of the fermenter vessels was inoculated with 5 ml of the 10% w/v fecal suspension. An aliquot of the fecal suspension (sample S) was also taken for analysis A 375 µl sample of the fecal suspension (sample S) or of each fermenter sample was required in duplicate for bacterial counts by FISH. Each sample was fixed by mixing thoroughly in 1.125 ml cold, filtered 4% (w/v) paraformaldehyde solution in PBS pH7.2) and storing at 4° C. overnight (or at least 4 hours).

The fixed sample was centrifuged at 13,000×g for 5 minutes and the supernatant discarded. The pellet was washed twice by re-suspending in 1 ml of cold, filtered 1×PBS, each time pelleting the cells by centrifugation and discarding the supernatant. The pellet was finally re-suspended thoroughly in 150 µl of filtered PBS; 150 µl of 96% (v/v) ethanol is then mixed in well. The cell preparation was then stored at −20° C. for at least 1 h before further processing.

In the hybridization step, 16 µl of the cell preparation (brought to ambient temperature) was mixed with 200 µl filtered, pre-warmed 2× hybridization buffer (30.3 mM Tris-HCl pH 7.2, 1.4 mM NaCl) containing 15.1 ml/l 10% (w/v) SDS. This mixture was warmed to the appropriate hybridization temperature and then mixed with the probe (50 ng/µl) in the ratio 9:1, respectively. The hybridization preparation was then returned to the hybridization oven to incubate overnight.

Finally, the hybridized cell preparations were collected onto 0.2 µm filters for microscopic observation, Depending upon cell density, between 5 µl and 100 µl of the cell preparation was added to filtered, pre-warmed (to hybridization temperature) washing buffer (5-7 ml 20 mM Tris-HCl pH 7.2, 0.9 M NaCl). 20 µl DAPI (4', 6-diamidino-2-phenylindole) was also added to the mixture to stain all cells and obtain total cell counts for each sample. This was then vacuum-filtered onto a 0.2 m polycarbonate filter and placed on a microscope slide. To minimize fading of the fluorescent dye, a drop of SlowFade™ (Molecular Probes) was placed on the filter and covered with a cover slip; the slides were then stored in the dark at 4° C. until used. Bacteria tagged with a Cy3 fluorescent probe were counted using fluorescence microscopy (Leitz, Wetzlar, Germany) at 550 nm; UV light was used for counting DAPI stained bacteria. Bacteria were counted in at least 15 fields taken at random and the average of these used to estimate the number of cells per ml of the original sample.

Four comparison, fermentation tests were run as listed below.

TABLE 4

Fermentation Runs

| Fermentation Run | Test Substances | |
|---|---|---|
| F1 | FOS | |
| F2 | Human Milk | PDX |
| F3 | GOS | |
| F4 | 1:1 LOS:GOS | 1:1 PDX:LOS |
| F5 | LOS | 1:1 PDX:GOS |

Example 7

This example illustrates the effect of PDX on the population and species of bacteria in the infant gut. In fermentation run 1 (F1), FOS was added to the formula feed and run in a fermenter system. FOS, which has traditionally been considered a good prebiotic ingredient, resulted in increases in *Bifidobacterium* spp. and *Clostridium* spp. and decreases in *Lactobacillus* spp. and *Bacteroides* spp. in V1. The addition of FOS to formula feed resulted in no change in *Bifidobacterium* spp. and *Lactobacillus* spp. levels and increases in *Clostridium* spp. and *Bacteroides* spp. in V2.

In F2, PDX and human milk were run in parallel fermenter systems. Human milk samples were provided by a maternity ward and stored frozen. These were early milk samples of varying volumes from several donors. The human milk feed was run without dilution or addition of lactose in order to maintain comparable levels of oligosaccharides and other nutrients. There was insufficient human milk to run this fermenter for 12 days, in parallel with the PDX fermenter. More frequent samples were therefore taken, at days 0, 4, 6 and 8. For comparative purposes, additional samples were taken from the PDX fermenter at day 8, and also at day 11.

As would be expected, human milk promoted good growth of beneficial bacteria, both bifidobacteria and lactobacilli, and decreased clostridia levels, as shown in FIG. 17. Bifidobacteria and lactobacilli clearly increased in population in both vessels. *Bacteroides* numbers remained at a similar level throughout the fermentation.

The results of PDX addition to the formula feed were also favorable, with a marked increase in lactobacilli and decreases in both clostridia and *bacteroides* in both vessels (FIG. 17).

In F3, GOS was added to the formula feed and run in a fermenter system. The addition of GOS to the formula feed had little apparent effect on lactobacilli in either vessel, but increased bifidobacteria in V1 and V2, and decreased clostridia and *bacteroides* in V1 but not V2.

The combination of LOS:GOS (1:1) was run against 1:1 PDX:LOS in a parallel fermenter system during F4. The LOS:GOS combination was effective in increasing numbers of lactobacilli in both vessels and bifidobacteria in V1, and in decreasing *bacteroides* in V1. Clostridia decreased in V2 but increased in V1.

Supplementation of the formula feed with a 1:1 combination of PDX:LOS resulted in an increase in lactobacilli in V1, but a slight decrease in bifidobacteria in each vessel. Clostridia tended to decrease in both vessels which *bacteroides* decreased mainly in V2.

In F5, LOS was supplemented into the formula feed and run in a parallel fermenter system against a 1:1 combination of PDX and GOS. The addition of LOS to the formula feed increased lactobacilli in both vessels. However, clostridia also increased in V2 and bifidobacteria decreased in both vessels. Although *bacteroides* decreased in V1 this was not maintained in V2. The addition of PDX:GOS to the formula feed increased levels of bifidobacteria and lactobacilli in both vessels, but also caused clostridia levels to increase. *Bacteroides* levels increased in V2 only.

Overall, bifidobacteria increased in proportion to the total bacterial population in V1 with human milk, GOS, FOS, PDX and the PDX:GOS combination. In V2, GOS, the PDX:GOS combination and the LOS:GOS combination led to an increase in bifidobacteria. Clostridia decreased in proportion to the total population in V1 with human milk, GOS and PDX, and decreased in V2 with human milk, PDX and the LOS:GOS combination.

In V1, the lactobacilli showed an increase following supplementation with LOS, PDX, human milk or PDX combinations, whereas increases in lactobacilli were observed in V2 with LOS, PDX, human milk, and GOS combinations. The increases in the percentage of lactobacilli were particularly marked with PDX and the PDX:GOS combination and the LOS:GOS combination in V2.

Overall, PDX was effective in increasing lactobacilli and decreasing levels of clostridia and *bacteroides*, with only slight increases in bifidobacteria in V1. The PDX:GOS combination also looked favorable for bifidobacteria, which increased amongst the total bacteria (although not as a percentage of the four groups) and increased lactobacilli at a pH of 5.2, but it also had the unfavorable effect of increasing *bacteroides* numbers.

When human milk was tested in the model system designed by the inventors, bifidobacteria and lactobacilli levels increased in number, while clostridia decreased in number. This effect was most consistently duplicated with PDX, and with GOS, either alone or in combination with LOS or PDX. FOS, which is another carbohydrate that is currently utilized in various infant formulas, was tested and did not produce the same desirable results.

Example 8

This example illustrates one embodiment of an infant formula of the present invention.

TABLE 5

Nutrient Information for Infant formula

| Ingredient | Per 10,000 L |
|---|---|
| Demineralized Whey Solids | 534.337 kg |
| Fat Blend | 339.695 kg |

TABLE 5-continued

Nutrient Information for Infant formula

| Ingredient | Per 10,000 L |
|---|---|
| Nonfat Milk Solids | 191.234 kg |
| Lactose | 136.321 kg |
| Galactooligosaccharide Syrup Solid | 35.096 kg |
| Polydextrose | 22.222 kg |
| Potassium Citrate | 7.797 kg |
| Mono- and Diglycerides | 7.233 kg |
| Single Cell Arachidonic Acid Oil | 6.486 kg |
| Calcium Phosphate, Tribasic | 4.185 kg |
| Ascorbic Acid | 1,403.323 g |
| Sodium Ascorbate | 1,168.402 g |
| Inositol | 407.029 g |
| Taurine | 402.962 g |
| Corn Syrup Solids | 188.300 g |
| Niacinamide | 89.857 g |
| Calcium Pantothenate | 42.443 g |
| Vitamin $B_{12}$ | 23.613 g |
| Biotin Trituration | 23.613 g |
| Thiamin HCl | 8.022 g |
| Pyridoxine HCl | 6.176 g |
| Folic Acid | 2.260 g |
| Lecithin Concentrate | 3.694 kg |
| Single Cell Docosahexaenoic Acid Oil | 3.243 kg |
| Carrageenan | 2.826 kg |
| Calcium Chloride | 2.650 kg |
| Sodium Chloride | 1.410 kg |
| Maltodextrin | 484.199 g |
| CMP, free acid | 151.951 g |
| AMP, free acid | 33.944 g |
| GMP, disodium salt | 18.347 g |
| UMP, disodium salt | 7.559 g |
| Ferrous Sulfate | 0.620 kg |
| Sodium Citrate | 0.455 kg |
| Tocopheryl Acetate, DL-Alpha | 160.882 g |
| Soy Oil | 139.612 g |
| Vitamin A Palmitate | 17.253 g |
| Cholecalciferol Concentrate | 5.715 g |
| Vitamin K, Liquid Phytonadione | 0.538 g |
| Zinc Sulfate | 214.225 g |
| Sodium Selenite | 51.112 g |
| Cupric Sulfate | 22.885 g |
| Lactose | 12.659 g |
| Manganese Sulfate | 3.119 g |
| Water, Deflouridated | 10,311.900 kg |

LOS is generated when lactose is heated at a high temperature. Therefore, in this embodiment the product contains indigenous LOS. The level of indigenous LOS in the product is approximately 2 g/L.

Example 9

This example illustrates another embodiment of an infant formula of the present invention.

TABLE 6

Nutrient Information for Infant formula

| Ingredient | Per 10,000 L |
|---|---|
| Demineralized Whey Solids | 534.337 kg |
| Fat Blend | 339.695 kg |
| Nonfat Milk Solids | 191.234 kg |
| Lactose | 142.000 kg |
| Galactooligosaccharide Syrup Solid | 23.164 kg |
| Polydextrose | 22.222 kg |
| Lactulose Syrup Solid | 10.353 kg |
| Potassium Citrate | 7.797 kg |
| Mono- and Diglycerides | 7.233 kg |
| Single Cell Arachidonic Acid Oil | 6.486 kg |
| Calcium Phosphate, Tribasic | 4.185 kg |

TABLE 6-continued

Nutrient Information for Infant formula

| Ingredient | Per 10,000 L |
|---|---|
| Ascorbic Acid | 1,403.323 g |
| Sodium Ascorbate | 1,168.402 g |
| Inositol | 407.029 g |
| Taurine | 402.962 g |
| Corn Syrup Solids | 188.300 g |
| Niacimamide | 89.857 g |
| Calcium Pantothenate | 42.443 g |
| Vitamin $B_{12}$ | 23.613 g |
| Biotin Trituration | 23.613 g |
| Thiamin HCl | 8.022 g |
| Pyridoxine HCl | 6.176 g |
| Folic Acid | 2.260 g |
| Lecithin Concentrate | 3.694 kg |
| Single Cell Docosahexaenoic Acid Oil | 3.243 kg |
| Carrageenan | 2.826 kg |
| Calcium Chloride | 2.650 kg |
| Sodium Chloride | 1.410 kg |
| Maltodextrin | 484.199 g |
| CMP, free acid | 151.951 g |
| AMP, free acid | 33.944 g |
| GMP, disodium salt | 18.347 g |
| UMP, disodium salt | 7.559 g |
| Ferrous Sulfate | 0.620 kg |
| Sodium Citrate | 0.455 kg |
| Tocopheryl Acetate, DL-Alpha | 160.882 g |
| Soy Oil | 139.612 g |
| Vitamin A Palmitate | 17.253 g |
| Cholecalciferol Concentrate | 5.715 g |
| Vitamin K, Liquid Phytonadione | 0.538 g |
| Zinc Sulfate | 214.225 g |
| Sodium Selenite | 51.112 g |
| Cupric Sulfate | 22.885 g |
| Lactose | 12.659 g |
| Manganese Sulfate | 3.119 g |
| Water, Deflouridated | 10,311.900 kg |

LOS is generated when lactose is heated at a high temperature. Therefore, in this embodiment the product contains both added and indigenous LOS. The total level of LOS in the product, including both added and indigenous LOS, is approximately 2.6 g/L.

Example 10

This example illustrates yet another embodiment of an infant formula of the present invention.

TABLE 7

Nutrient Information for Infant formula

| Ingredient | Per 10,000 L |
|---|---|
| Demineralized Whey Solids | 534.337 kg |
| Fat Blend | 339.695 kg |
| Nonfat Milk Solids | 191.234 kg |
| Lactose | 119.321 kg |
| Galactooligosaccharide Syrup Solid | 46.327 kg |
| Polydextrose | 44.444 kg |
| Lactulose Syrup Solid | 20.706 kg |
| Potassium Citrate | 7.797 kg |
| Mono- and Diglycerides | 7.233 kg |
| Single Cell Arachidonic Acid Oil | 6.486 kg |
| Calcium Phosphate, Tribasic | 4.185 kg |
| Ascorbic Acid | 1,403.323 g |
| Sodium Ascorbate | 1,168.402 g |
| Inositol | 407.029 g |
| Taurine | 402.962 g |
| Corn Syrup Solids | 188.300 g |
| Niacimamide | 89.857 g |
| Calcium Pantothenate | 42.443 g |

TABLE 7-continued

Nutrient Information for Infant formula

| Ingredient | Per 10,000 L |
|---|---|
| Vitamin $B_{12}$ | 23.613 g |
| Biotin Trituration | 23.613 g |
| Thiamin HCl | 8.022 g |
| Pyridoxine HCl | 6.176 g |
| Folic Acid | 2.260 g |
| Lecithin Concentrate | 3.694 kg |
| Single Cell Docosahexaenoic Acid Oil | 3.243 kg |
| Carrageenan | 2.826 kg |
| Calcium Chloride | 2.650 kg |
| Sodium Chloride | 1.410 kg |
| Maltodextrin | 484.199 g |
| CMP, free acid | 151.951 g |
| AMP, free acid | 33.944 g |
| GMP, disodium salt | 18.347 g |
| UMP, disodium salt | 7.559 g |
| Ferrous Sulfate | 0.620 kg |
| Sodium Citrate | 0.455 kg |
| Tocopheryl Acetate, DL-Alpha | 160.882 g |
| Soy Oil | 139.612 g |
| Vitamin A Palmitate | 17.253 g |
| Cholecalciferol Concentrate | 5.715 g |
| Vitamin K, Liquid Phytonadione | 0.538 g |
| Zinc Sulfate | 214.225 g |
| Sodium Selenite | 51.112 g |
| Cupric Sulfate | 22.885 g |
| Lactose | 12.659 g |
| Manganese Sulfate | 3.119 g |
| Water, Deflouridated | 10,325.600 kg |

LOS is generated when lactose is heated at a high temperature. Therefore, in this embodiment the product contains both added and indigenous LOS. The total level of LOS in the product, including both added and indigenous LOS, is approximately 3.6 g/L.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A nutritional formula capable of increasing the population of Bifidobacteria in the human gut, comprising
   a. a lipid or fat;
   b. a protein source selected from the group consisting of whey protein, casein, casein protein, nonfat milk, hydrolyzed protein and combinations thereof;
   c. about 5 to about 200 mg/100 kcal of a source of long chain polyunsaturated fatty acids; and d. about 1.0 to about 10.0 g/L of a prebiotic composition, wherein the prebiotic composition comprises at least 20% of an oligosaccharide which comprises galacto-oligosaccharide, and further wherein the oligosaccharide also comprises polydextrose.

2. The nutritional formula of claim 1, wherein the source of long chain polyunsaturated fatty acids comprises docosahexanoic acid, arachidonic acid or combinations thereof.

3. The nutritional formula of claim 2, wherein the source of long chain polyunsaturated fatty acids comprises docosahexanoic acid and arachidonic acid, further wherein the ratio of arachidonic acid to docosahexanoic acid is from about 1:3 to about 9:1.

4. The nutritional formula of claim 1, wherein the lipid or fat is present at a level of about 3 to about 7 g/100 kcal.

5. The nutritional formula of claim 1, wherein the protein source is present at a level of about 1 to about 5 g/100 kcal.

6. The nutritional formula of claim 1, which further comprises at least one probiotic.

7. The nutritional formula of claim 6, wherein the probiotic is selected from the group consisting of *Bifidobacteria* spp., *Lactobacillus* spp and combinations thereof.

8. A nutritional formula capable of producing an improved short chain fatty acid profile in the gut, comprising
    a. a lipid or fat;
    b. a protein source selected from the group consisting of whey protein, casein, casein protein, nonfat milk, hydrolyzed protein and combinations thereof;
    c. about 5 to about 200 mg/100 kcal of a source of long chain polyunsaturated fatty acids;
    d. about 1.0 to about 10.0 g/L of a prebiotic composition, wherein the prebiotic composition comprises at least 20% of an oligosaccharide which comprises galacto-oligosaccharide and further wherein the prebiotic composition further comprises polydextrose; and
    e. at least one probiotic.

9. The nutritional formula of claim 8, wherein the short chain fatty acid profile comprises an increased production of acetate.

10. The nutritional formula of claim 8, wherein the short chain fatty acid profile comprises a decreased production of butyrate.

11. The nutritional formula of claim 8, wherein the source of long chain polyunsaturated fatty acids comprises docosahexanoic acid, arachidonic acid or combinations thereof.

12. The nutritional formula of claim 11, wherein the source of long chain polyunsaturated fatty acids comprises docosahexanoic acid and arachidonic acid, further wherein the ratio of arachidonic acid to docosahexanoic acid is from about 1:3 to about 9:1.

13. The nutritional formula of claim 8, wherein the probiotic is selected from the group consisting of *Bifidobacteria* spp., *Lactobacillus* spp and combinations thereof.

14. An infant formula, comprising
    a. a lipid or fat;
    b. a protein source selected from the group consisting of whey protein, casein, casein protein, nonfat milk, hydrolyzed protein and combinations thereof;
    c. about 5 to about 200 mg/100 kcal of a source of long chain polyunsaturated fatty acids;
    d. about 1.0 to about 10.0 g/L of a prebiotic composition, wherein the prebiotic composition comprises at least 20% of an oligosaccharide which comprises galacto-oligosaccharide and further wherein the prebiotic composition further comprises polydextrose; and
    e. at least one probiotic.

15. The infant formula of claim 14, wherein the source of long chain polyunsaturated fatty acids comprises docosahexanoic acid, arachidonic acid or combinations thereof.

16. The infant formula of claim 15, wherein the source of long chain polyunsaturated fatty acids comprises docosahexanoic acid and arachidonic acid, further wherein the ratio of arachidonic acid to docosahexanoic acid is from about 1:3 to about 9:1.

17. The infant formula of claim 14, wherein the lipid or fat is present at a level of about 3 to about 7 g/100 kcal.

18. The infant formula of claim 14, wherein the protein source is present at a level of about 1 to about 5 g/100 kcal.

19. The infant formula of claim 14, wherein the probiotic is selected from the group consisting of *Bifidobacteria* spp., *Lactobacillus* spp and combinations thereof.

* * * * *